(12) United States Patent
Wang et al.

(10) Patent No.: US 10,301,203 B2
(45) Date of Patent: *May 28, 2019

(54) CHLOROPEROXIDASE-CATALYZED DEGRADATION OF PHARMACEUTICAL POLLUTANTS IN WASTEWATER

(71) Applicants: Xiaotang Wang, Hollywood, FL (US); Qinghao He, Miami, FL (US)

(72) Inventors: Xiaotang Wang, Hollywood, FL (US); Qinghao He, Miami, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/913,419

(22) Filed: Mar. 6, 2018

(65) Prior Publication Data

US 2018/0346360 A1 Dec. 6, 2018

Related U.S. Application Data

(63) Continuation of application No. 15/609,452, filed on May 31, 2017, now Pat. No. 9,938,176.

(51) Int. Cl.
*C02F 1/72* (2006.01)
*C02F 1/76* (2006.01)
(Continued)

(52) U.S. Cl.
CPC .............. *C02F 3/342* (2013.01); *C02F 1/722* (2013.01); *C02F 1/76* (2013.01);
(Continued)

(58) Field of Classification Search
CPC .. C02F 1/72; C02F 1/722; C02F 1/725; C02F 1/76; C02F 1/766; C02F 3/12;
(Continued)

(56) References Cited

U.S. PATENT DOCUMENTS

| 4,937,192 A | * | 6/1990 | Hunter | ................. C12N 9/0065 435/131 |
| 5,888,505 A | | 3/1999 | Allen | |

(Continued)

OTHER PUBLICATIONS

Libby et al., "Chloroperoxidase Halogenation Reactions: Chemical versus enzymic halogenating intermediates," The Journal of Biological Chemistry, vol. 257, No. 9, (1982), pp. 5030-5037. (Year: 1982).*

(Continued)

*Primary Examiner* — Lucas A Stelling
(74) *Attorney, Agent, or Firm* — Saliwanchik, Lloyd & Eisenschenk

(57) ABSTRACT

The present invention provides efficient, economical, and environmentally-friendly compositions and methods for removing pollutants from water sources. In particular embodiments, the present invention provides compositions and methods for catalyzing the degradation of pharmaceutical pollutants in wastewater using the enzyme chloroperoxidase (CPO). Another embodiment provides a method of degrading pollutants in wastewater and other water sources. In specific embodiments, the claimed composition and method can be used to degrade pharmaceutical pollutants selected from the group consisting of: acetaminophen, carbamazepine, sulfamethazine, diclofenac, and naproxen.

18 Claims, 41 Drawing Sheets

(51) Int. Cl.
- C02F 3/34 (2006.01)
- C02F 101/38 (2006.01)
- C02F 101/34 (2006.01)
- C02F 101/36 (2006.01)

(52) U.S. Cl.
CPC ......... *C12Y 111/0101* (2013.01); *C02F 1/725* (2013.01); *C02F 1/766* (2013.01); *C02F 2101/34* (2013.01); *C02F 2101/36* (2013.01); *C02F 2101/38* (2013.01); *C02F 2101/40* (2013.01)

(58) Field of Classification Search
CPC .. C02F 3/342; C02F 2101/34; C02F 2101/36; C02F 2101/38; C02F 2101/40; C12Y 111/0101
See application file for complete search history.

(56) References Cited

U.S. PATENT DOCUMENTS

| | | | |
|---|---|---|---|
| 6,251,386 B1 | 6/2001 | Johansen | |
| 2002/0119136 A1* | 8/2002 | Johansen | A01N 63/00 424/94.4 |
| 2003/0141256 A1 | 7/2003 | Sarkar et al. | |

OTHER PUBLICATIONS

Libby et al., "Defining the Involvement of HOCL or CL2 as Enzyme-generated Intermediates in Chloroperoxidase-catalyzed Reactions," The Journal of Biological Chemistry, vol. 267, No. 3, (1992), pp. 1769-1775 (Year: 1992).*

Aresta, A. et al., "Profiling urinary metabolites of naproxen by liquid chromatography-electrospray mass spectrometry." Journal of Pharmaceutical and Biomedical Analysis, 2006, 41: 1312-1316.

Ayala, M. et al., "Heme destruction, the main molecular event during the peroxide-mediated inactivation of chloroperoxidase from Caldariomyces fumago." J. Biol. Inorg. Chem., 2011, 16: 63-68.

Hager, L. P. et al., The Journal of Biological Chemistry, Apr. 1966, 241 (8): 1769-1777.

He, Q., "The Degradation of Pharmaceutical Pollutants in Wastewater Catalyzed by Chloroperoxidase and the Construction of Chloroperoxidase H105R Mutant." FIU Electronic Theses and Dissertations [online], 2016, [retrieved on Jul. 14, 2017]. Retrieved from the Internet<URL: http://digitalcommons.fiu.edu/etd/2540/>.

Hofrichter, M., Ullrich, R., "Oxidation catalyzed by fungal peroxygenases." Current Opinion in Chemical Biology, 2014, 19: 116-125.

Hofrichter, M., Ullrich, R., "Heme-thiolate haloperoxidases: versatile biocatalysts with biotechnological and environmental significance." Appl. Microbiol. Biotechnol., 2006, 71: 276-288.

Kedderis, G. L. et al., "N-Demethylation Reactions Catalyzed by Chloroperoxidase." The Journal of Biological Chemistry, Nov. 1980, 255 (21): 10174-10182.

Kinne, M. et al., "Regioselective preparation of 5-hydroxypropanolol and 4'-hydroxydiclofenac with a fungal peroxygenase." Bioorganic & Medicinal Chemistry Letters, 2009, 19: 3085-3087.

Libby, R. D. et al., "Defining the Involvement of HOCl or Cl2 as Enzyme-generated Intermediates in Chloroperoxidase-catalyzed Reactions." The Journal of Biological Chemistry, 1992, 267 (3): 1769-1775.

Libby, R. D. et al., "Chloroperoxidase Halogenation Reactions." The Journal of Biological Chemistry, May 1982, 257 (9): 5030-5037.

Manoj, K. M., "Chlorinations catalyzed by chloroperoxidase occur via diffusible intermediate(s) and the reaction components play multiple roles in the overall process." Biochimica et Biophysica Acta, 2006, 1764: 1325-1339.

Manoj, K. M. et al., "Explaining the Atypical Reaction Profiles of Heme Enzymes with a Novel Mechanistic Hypothesis and Kinetic Treatment." PLOS One, May 2010, 5 (5): 1-9.

Marco-Urrea, E. et al., "Degaradtion of the drug sodium diclofenac by Trametes versicolor pellets and identification of some intermediates by NMR." Journal of Hazardous Materials, 2010, 176: 836-842.

Meunier, B. et al., "Mechanism of Oxidation Reactions Catalyzed by Cytochrome P450 Enzymes." Chem. Rev., 2004, 104: 3947-3960.

Morris, D. R., Hager, L. P., "Chloroperoxidase I. Isolation and Properties of the Crystalline Glycoprotein." The Journal of Biological Chemistry, Apr. 1966, 241 (8): 1763-1768.

Osorio, V. et al., "Simultaneous determination of diclofenac, its human metabolites and microbial nitration/nitrosation transformation products in wastewaters by liquid chromatography/quadrupole-linear ion trap mass spectrometry." Journal of Chromatography A, 2014, 1347: 63-71.

Potter, D. W. et al., "Identification of Acetaminophen Polymerization Products Catalyzed by Horseradish Peroxidase." The Journal of Biological Chemistry, Oct. 1985, 260 (22): 12174-12180.

Sundaramoorthy, M. et al., "The crystal structure of chloroperoxidase: a heme peroxidase-cytochrome P45 functional hybrid." Structure, 1995, 3 (12): 1367-1377.

Vázquez-Duhalt, R. et al., "Biocatalytic chlorination of aromatic hydrocarbons by chloroperoxidase of Caldariomyces fumago." Phytochemistry, 2001, 58: 929-933.

Wang, X. et al., "Two-dimensional NMR Study of the Heme Active Site Structure of Chloroperoxidase." The Journal of Biological Chemistry, Mar. 2003, 278 (10): 7765-7774.

Wojcieszyńska, D. et al., "Bacterial degradation of naproxen—Undisclosed pollutant in the environment." Journal of Environmental Management, 2014, 145: 157-161.

Yi, X. et al., "Examining the Role of Flutamic Acid 183 in Chloroperoxidase Catalysis." The Journal of Biological Chemistry, Apr. 2003, 278 (16): 13855-13859.

* cited by examiner

| Code | Formula | Retention time (min) | Experimental mass (m/z) | Theoretical mass (m/z) | Diff (ppm) | Diff (mDa) |
|---|---|---|---|---|---|---|
| APAP | $C_8H_9NO_2$ | 2.986 | 151.0623 | 151.0633 | -7.06 | -1.07 |
| AM1 | $C_8H_8ClNO_2$ | 3.713 | 185.0244 | 185.0246 | 1.27 | 0.23 |
| AM2 | $C_{16}H_{16}N_2O_4$ | 3.436 | 300.1110 | 300.1115 | 1.59 | 0.48 |
| AM3 | $C_{16}H_{15}ClN_2O_4$ | 4.157 | 334.0720 | 334.0724 | 1.12 | 0.38 |
| AM4 | $C_8H_7Cl_2NO_2$ | 4.822 | 218.9854 | 218.9847 | -3.23 | -0.71 |
| AM5 | $C_{16}H_{14}Cl_2N_2O_4$ | 4.673 | 368.0331 | 368.0328 | -0.82 | -0.30 |
| AM6 | $C_{24}H_{23}N_3O_6$ | 4.051 | 449.1578 | 449.1587 | -1.94 | -0.87 |
| AM7 | $C_{24}H_{22}ClN_3O_6$ | 4.567 | 483.1200 | 483.1197 | 0.59 | 0.29 |

FIG. 11

$C_8H_9NO_2$ (APAP)

$C_8H_8ClNO_2$ (AM1)

$C_{16}H_{16}N_2O_4$ (AM2)

$C_{16}H_{15}ClN_2O_4$ (AM3)

$C_8H_7Cl_2NO_2$ (AM4)

$C_{16}H_{14}Cl_2N_2O_4$ (AM5)

$C_{24}H_{23}N_3O_6$ (AM6)

$C_{24}H_{22}ClN_3O_6$ (AM7)

| $K_m$ (μM) | $V_{max}$ (μM s$^{-1}$) | $k_{cat}$ (s$^{-1}$) | $k_{cat}/K_m$ (μM$^{-1}$s$^{-1}$) | $R^2$ |
|---|---|---|---|---|
| 73.35 | 3.87 | 733 | 10.54 | 0.9995 |

FIG. 18

$C_{15}H_{12}N_2O$ (CBZ)     $C_{15}H_{12}N_2O_2$ (CM1)

$C_{15}H_{14}N_2O_3$ (CM2)     $C_{14}H_{11}NO_2$ (CM3)

$C_{14}H_9NO$ (CM4)     $C_{13}H_9N$ (CM5)

$C_{13}H_9NO$ (CM6)     $C_{15}H_{13}NO_2$ (CM7)

| Precursor ion | | Precursor ion (m/z) | Shared product ions (m/z) | Independent product ions (m/z) |
|---|---|---|---|---|
| $C_{14}H_9NO$ | (CM4) | 208 | 180, *152*, *128*, *127*, 77, 101, 51 | 75, 102, *154*, |
| $C_{13}H_9N$ | (CM5) | 180 | | 75, 102, *153*, 140 |
| $C_{15}H_{13}NO_2$ | (CM7) | 240 | | 208, *153*, *154* |

FIG. 22

| Code | Formula | Retention time (min) | Experimental mass (m/z) | Theoretical mass (m/z) | Diff (ppm) | Diff (mDa) |
|---|---|---|---|---|---|---|
| SMZ | $C_{12}H_{14}N_4O_2S$ | 4.245 | 278.0832 | 278.0837 | -1.93 | -0.54 |
| SM1 | $C_{12}H_{14}N_4$ | 3.219 | 214.1211 | 214.1218 | -3.27 | -0.70 |
| SM2 | $C_{12}H_{13}ClN_4$ | 4.106 | 248.0829 | 248.0829 | 0.00 | 0.00 |
| SM3 | $C_{12}H_{12}Cl_2N_4$ | 7.295 | 282.0440 | 282.0439 | 0.23 | 0.07 |
| SM4 | $C_{12}H_{11}Cl_3N_4$ | 7.400 | 316.0044 | 316.0049 | -1.71 | -0.54 |
| SM5 | $C_{12}H_{13}ClN_4O_2S$ | 4.894 | 312.0447 | 312.0448 | -0.13 | -0.04 |
| SM6 | $C_{12}H_{12}Cl_2N_4O_2S$ | 5.414 | 346.0054 | 346.0058 | -1.04 | -0.36 |
| SM7 | $C_{12}H_{13}ClN_4O_3S$ | 2.980 | 328.0398 | 328.0397 | 0.25 | 0.08 |
| SM8 | $C_{12}H_{11}Cl_3N_4O2S$ | 7.267 | 379.9668 | 379.9668 | -0.16 | -0.06 |
| SM9 | $C_{12}H_{14}N_4O_3S$ | 1.020 | 294.0790 | 294.0787 | 1.17 | 0.34 |

FIG. 25

| Code | Formula | Retention time (min) | Experimental mass (m/z) | Theoretical mass (m/z) | Diff (ppm) | Diff (mDa) |
|---|---|---|---|---|---|---|
| SM5-Br | $C_{12}H_{13}BrN_4O_2S$ | 5.390 | 355.9948 | 355.9943 | 1.65 | 0.59 |
| SM6-Br | $C_{12}H_{12}Br_2N_4O_2S$ | 6.095 | 433.9042 | 433.9048 | -1.28 | -0.55 |
| SM8-Br | $C_{12}H_{11}Br_3N_4O_2S$ | 8.258 | 511.8144 | 511.8153 | -1.66 | -0.85 |

FIG. 28

Chemical Formula: $C_{12}H_{14}N_4O_2S$
(SMZ)

Chemical Formula: $C_{12}H_{13}BrN_4O_2S$
(SM5-Br)

Chemical Formula: $C_{12}H_{12}Br_2N_4O_2S$
(SM6-Br)

Chemical Formula: $C_{12}H_{11}Br_3N_4O_2S$
(SM8-Br)

| substance | COD (mg·L$^{-1}$) | COD removal (%) | TOC (mg·L$^{-1}$) | TOC removal (%) |
|---|---|---|---|---|
| diclofenac | 41→39 | 4.9 | 8.3→6.2 | 25 |
| naproxen | 22→20 | 9.1 | 158→146 | 7.6 |

FIG. 37

CHLOROPEROXIDASE-CATALYZED DEGRADATION OF PHARMACEUTICAL POLLUTANTS IN WASTEWATER

CROSS-REFERENCE TO RELATE APPLICATION

This application is a continuation application of U.S. application Ser. No. 15/609,452, filed May 31, 2017, which is incorporated herein by reference in its entirety, including any figures, tables and drawing.

GOVERNMENT SUPPORT

This invention was made with government support under grant number CHE0540763, awarded by the National Science Foundation. The government has certain rights in the invention.

BACKGROUND OF INVENTION

Water systems are routinely monitored for the presence of pollutants, such as bacteria, viruses, pesticides, petroleum, acids, metals, and other chemicals. Increasingly, in recent years, pollution from prescription drugs and over-the-counter (OTC) medications has caused concern among water quality experts and environmental advocates. Pharmaceutical compounds have been detected in lakes, rivers, and streams, in amounts ranging from nanograms per liter to micrograms per liter. Even in small concentrations exposure to pharmaceutical pollutants has been shown to cause harm to aquatic ecosystems, such as, for example, altered sex ratios in certain fish populations. While the risk of low concentrations of pharmaceuticals in water appears to be minor for humans, sound information about the true effects and risks of chronic drug exposure due to pharmaceutical water pollution is lacking.

Pharmaceutical compounds that enter aquatic environments mainly come from human and veterinary medicines, such as antibiotics, antidepressants, blood thinners, hormones, and painkillers. Sometimes, unused or expired medications enter waterways as a result of improper disposal, for example, by flushing them down the toilet or drain. Pharmaceuticals can also enter water systems as a result of human and animal drug consumption. The body metabolizes only a fraction of most ingested drugs. The remainder is excreted through sweat, urine, or feces, which in turn ends up in wastewater systems. In the case of antibiotic- or hormone-fed livestock in large-scale feeding operations, these unmetabolized drug compounds can leach into groundwater from the tons of regularly produced manure. Furthermore, some medications are applied as creams or lotions rather than being ingested. The portions of these medications that are not absorbed into the skin are washed off into wastewater as well.

While there have been certain efforts to prevent improper disposal of pharmaceuticals, such as drug take-back programs and disposal guidelines from the federal Environmental Protection Agency (EPA), these efforts do not effectively capture all drugs that might be disposed of in water systems. Thus, wastewater treatment is an important measure to help remove those remaining pharmaceutical pollutants that do end up in the water.

There are multiple types of wastewater treatment. Activated sludge involves the use of air, bacteria, and/or protozoa to degrade organic materials and remove nutrients from sewage and industrial waste waters. However, the efficiency of the activated sludge process in removing pollutants varies based on, for example, the temperature of degradation and hydraulic retention time for the various drug compounds. Additionally, activated sludge systems consume large amounts of energy. Also, construction, maintenance, and operation can be costly.

Other conventional systems include biological filtration, which is often utilized for municipal wastewater. These methods are insufficient to eliminate all persistent pharmaceutical residues, however, because of the diversity of drug properties. Additionally, sewage treatment results in the production of semi-solid waste byproducts, which require further treatment before being suitable for disposal.

Advanced processes such as UV, ozonation, microfiltration, and ultrasound can achieve degradation of drug compounds close to, or at 100%, efficiency. Nevertheless, these methods are inconsistent as well because of the complexity of pharmaceutical pollutants.

Given the increase in pharmaceutical and personal care product use, it is unclear whether these existing efforts will be sufficient to combat pharmaceutical water pollution, due to limitations such as cost, efficiency, secondary byproducts, and inconsistency.

Thus, further investigations into the removal and/or breakdown of widely used drugs in the environment, as well as improved methods of treating drug contamination in water sources, are warranted to prevent potential long-term consequences to the health of humans, other living organisms, and the environment.

BRIEF SUMMARY

The present invention provides efficient, economical, and environmentally-friendly compositions and methods for removing pollutants from water sources. In particular embodiments, the present invention provides compositions and methods for degrading pharmaceutical pollutants in wastewater using the enzyme chloroperoxidase (CPO).

One embodiment of the subject invention provides a composition for the treatment of wastewater and other water sources comprising the enzyme chloroperoxidase, an oxidant, and a halogen ion. In one embodiment, the oxidant is hydrogen peroxide. In a further embodiment, the halogen ion is chloride or bromide.

In some embodiments, chloroperoxidase is in its pure form. The growth medium of *Caldariomyces fumago* functions similarly to the pure form of CPO. In other embodiments, chloroperoxidase is used in a more crude protein form.

Advantageously, the compositions of the subject invention can be used at low concentrations to degrade pharmaceutical pollutants in water. In specific embodiments, the pharmaceutical pollutants can be one or more drugs from the following classes: acetaminophen, carbamazepine, sulfamethazine, diclofenac, naproxen, or any other drug sharing similar structures with these compounds.

Another embodiment provides methods for degrading pollutants in wastewater or other polluted water sources comprising administering an effective amount of the composition to the wastewater or water source; allowing the composition to catalyze the degradation of pollutants within the wastewater or water source; and allowing the pollutants to become sufficiently degraded.

In one embodiment, the method of the subject invention can be used to degrade pharmaceutical pollutants.

BRIEF DESCRIPTION OF THE FIGURES

FIG. 11 shows a table listing Accurate-Mass LC-Q-TOF-MS data for identification of APAP and its metabolites.

FIG. 18 shows a table listing kinetic parameters of CPO-catalyzed degradation of CBZ.

FIG. 22 shows the optimizer data of CM4, CM5, and CM7. The bold values were the mass of precursor ions. The italic values were estimated as the same fragments adducted with varying hydrogens.

FIG. 25 shows a table listing the Accurate-Mass QTOF-LC/MS data for identification of SMZ and its metabolites catalyzed in a CPO—$H_2O_2$—$Cl^-$ system.

FIG. 28 shows Accurate-Mass LC-Q-TOF-MS data for identification of SMZ and its metabolites catalyzed by a CPO—$H_2O_2$—$Br^-$ system.

FIG. 37 shows a table listing elimination of COD and TOC by CPO-catalyzed oxidative degradation.

DETAILED DISCLOSURE

The present invention provides efficient, economical, and environmentally-friendly compositions and methods for treating wastewater polluted by pharmaceuticals. In particular embodiments, the present invention provides compositions and methods for degrading pharmaceutical pollutants in wastewater using the enzyme chloroperoxidase (CPO).

One embodiment of the subject invention provides a composition for treating wastewater or another source of water comprising remedially-effective amounts of each of: the enzyme chloroperoxidase, an oxidant, and a halogen ion, wherein the remedially-effective amounts are combined to form a system capable of degrading drug pollutants present in the wastewater or water source.

Chloroperoxidase Enzyme

Figure 1:
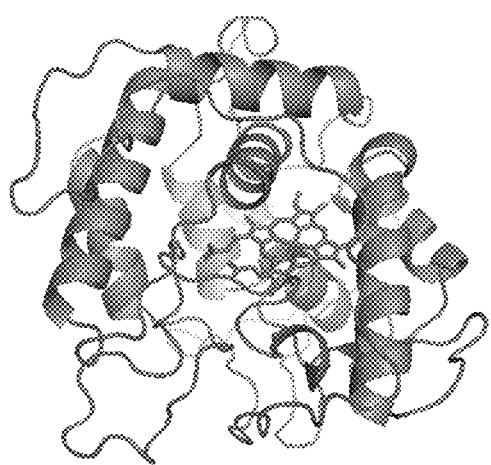
FIG. 1 shows the crystal structure of CPO, as represented by Pymol software (protein database (PDB) entry 1CPO). The heme prophryin, is the lattice-like structure located in the center of the protein.

Chloroperoxidase (CPO) is a heme-containing glycoprotein secreted by the fungus *Caldariomyces fumago*. FIG. 1 shows the crystal structure of CPO, with its heme porphyrin depicted in red at the center of the protein.

Figure 2:
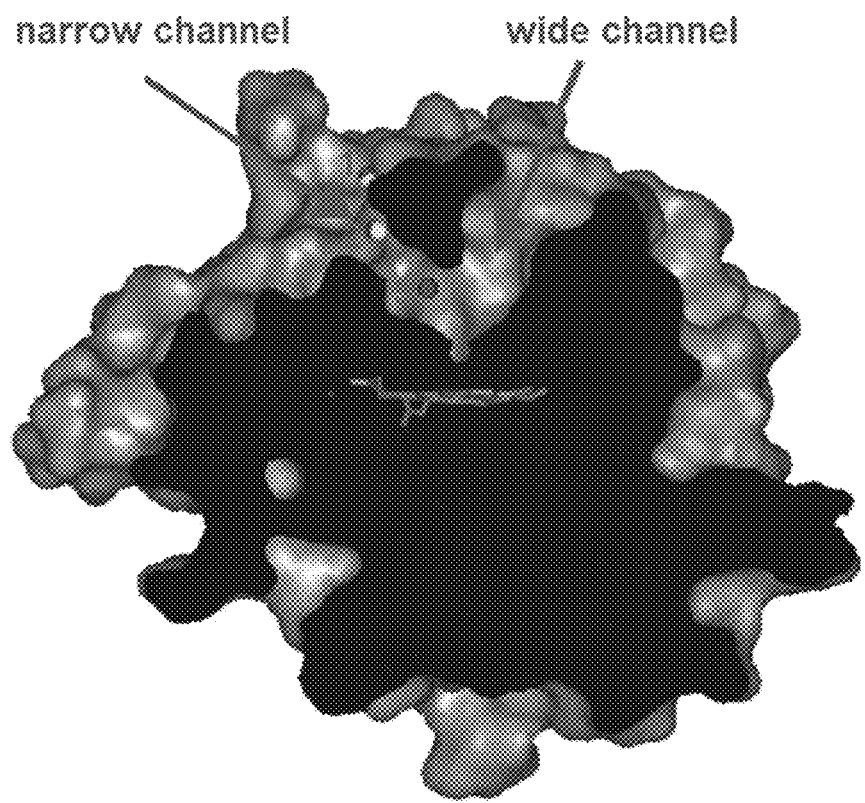
FIG. 2 shows a slice of CPO crystal structure with surface representation. The heme is the lighter-shaded structure depicted at the center. The narrow and wide channels are marked by arrows. Bromide is represented by lighter shaded spheres, adjacent to numbers 1 and 2. Iodide is represented by the darker spheres adjacent to numbers 1 through 3. The halide binding sites are labeled by numbers 1 through 3.

FIG. 2 shows a slice of the crystal structure of CPO. As depicted by arrows, there is a narrow channel connecting the protein surface to the heme center. Halogen ions, such as bromide and iodide, bind with sites in the narrow channel, suggesting that this channel provides the pathway for halides to reach the heme active center from the protein surface. In addition, the surface contains another, wider channel. This channel is likely the site where bulky molecules bind, and where reactions such as oxidation and epoxidation occur. Advantageously, CPO catalyzes two major types of oxidation: one-electron oxidations, similar to most peroxidases, and two-electron oxidations, which are rare for conventional peroxidases.

Figure 3:
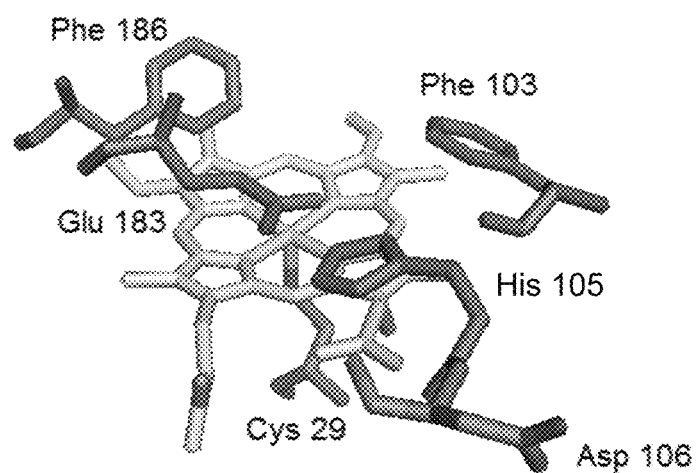
FIG. 3 shows the active site of CPO with important amino acids in the distal pocket, as represented by Pymol software (PDB entry 1CPO). The heme is depicted at the center. His 105 was proposed to form hydrogen bonds with Glu 183 and Asp 106, thus conferring the proper position of Glu183 for forming Compound I. Phe 103 and Phe 186 were observed in close proximity to the heme center, suggesting their control over substrate access to the heme center by polarity.

FIG. 3 shows a representation of the CPO active site. The heme active site of CPO resembles that of P450s and peroxidase. In conventional heme peroxidases, histidine residue acts as an acid-base catalyst. CPO differs in that it utilizes glutamic acid 108 (Glu 183).

Generally, in reactions catalyzed by heme peroxidases, the distal acid-base catalyst forms hydrogen bond networks with other amino acids to achieve the cleavage of the O—O bond of hydrogen peroxide. In CPO, Glu 183 reacts with histidine 105 (His 105). His 105 forms hydrogen bonds with Glu 183 and Asp 106, facilitating cleavage of the peroxide bond and proper positioning of Glu 183 in relation to the heme center. Two phenylalanine residues (Phe 103 and Phe 186) are in close proximity to the heme iron, and are thought to interact with hydrophobic substrates to control access to the heme center.

CPO-Catalyzed Reactions

The ability of CPO to catalyze one-electron oxidations, and two-electron oxidations, facilitates the use of CPO in the treatment of environmental pollution.

CPO-catalyzed one-electron oxidations include peroxidation, and dehalogenation/polymerization driven by radicals.

Figure 4:
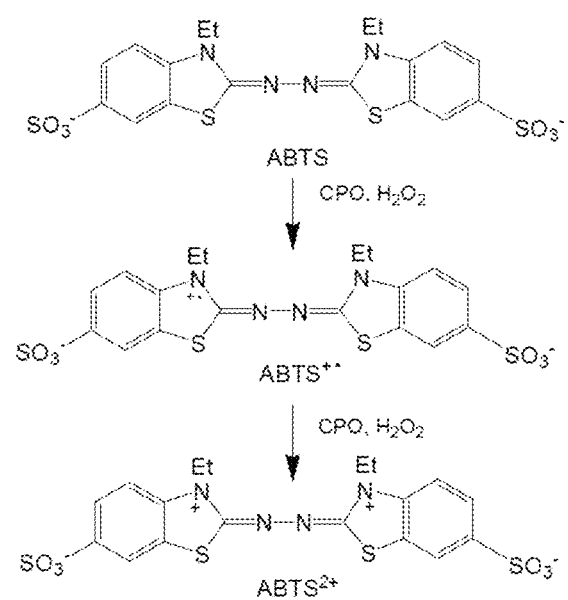
FIG. 4 shows the oxidation of 2,2'-azino-bis(3-ethylbenzothiazoline-6-sulfonic acid) (ABTS), catalyzed by CPO.

FIG. 4 shows the oxidation of 2,2'-azinobis-3-ethylbenzothiazoline-6-sulfonic acid (ABTS) catalyzed by CPO. This reaction typifies CPO-catalyzed peroxidation, and is used as an ABTS assay to measure the peroxidase activity of CPO and/or mutant strains of CPO.

Figure 5:
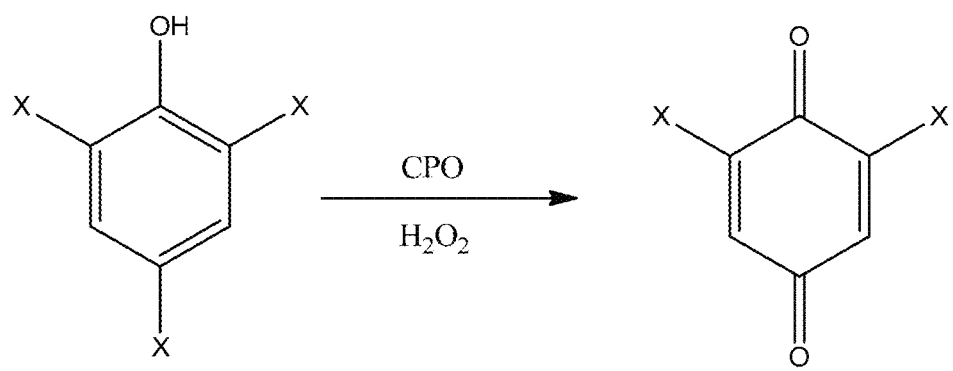
FIG. 5 shows the CPO-catalyzed dehalogenation of trihalophenols.

Additionally, dehalogenation has been found in trihalophenols and fluorophenols. FIG. 5 shows dehalogenation of trihalophenols catalyzed by CPO.

Figure 6:
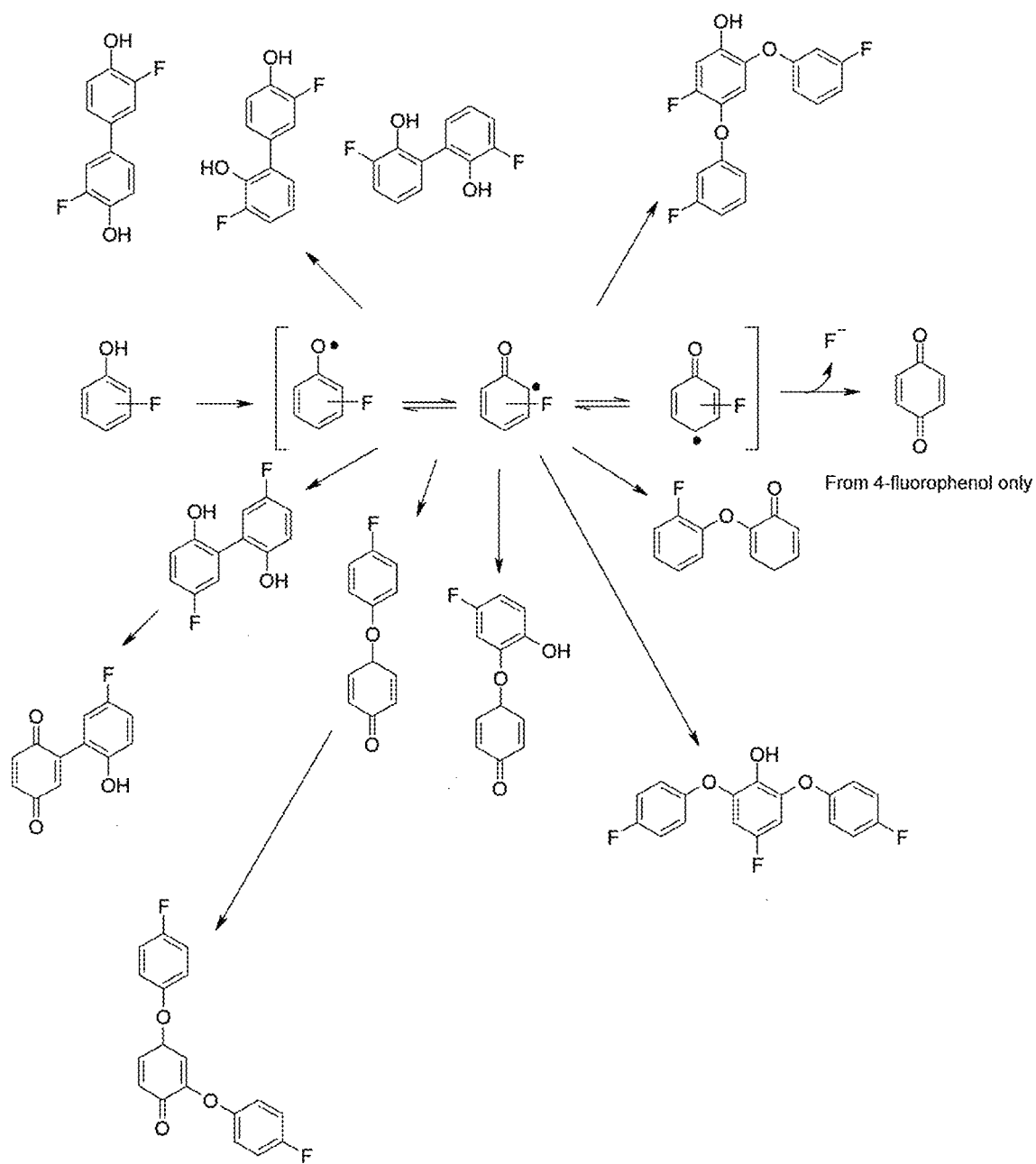
FIG. 6 shows the mechanism of CPO-catalyzed one-electron oxidation of fluorophenol.

FIG. 6 shows the mechanism of CPO-catalyzed one-electron oxidation of fluorophenols. According to this general mechanism, fluoride is not involved in CPO-catalyzed halogenation but is involved in dehalogenation. The function of polymerization shown by some other peroxidases is also found in CPO-catalyzed reactions. In the defluorination of fluorophenols, for example, dimers and trimers are generated.

Figure 7A:
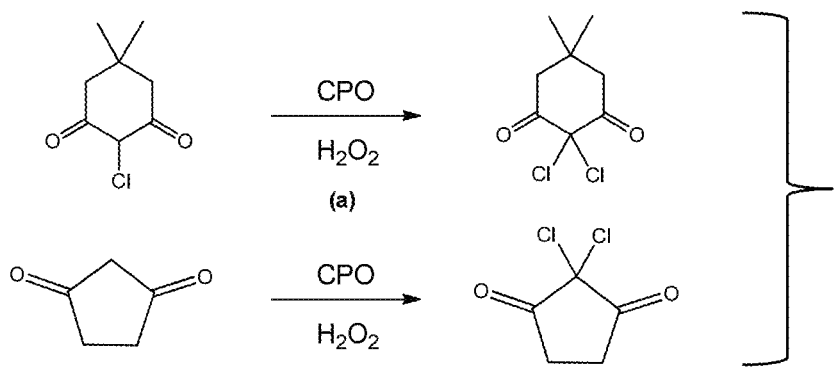
FIGS. 7A-7C show different examples of CPO-catalyzed reactions in phosphate buffer with chloride ions; 7A shows chlorination of monochlorodimedone (MCD); 7B shows halogenation by 1,3-cyclopentanedione and alkenes; 7C shows exemplary epoxidation and hydroxylation reactions, including yields and enantiomeric purities.

The two-electron oxidations catalyzed by CPO include halogenation and oxygen transfer. The reaction depicted in FIG. 7A shows CPO catalyzed chlorination of monochlorodimedone (MCD). This reaction is routinely used as an MCD assay to measure the chlorination activity of CPO and/or mutant strains of CPO. Halogenation can also be carried out by bromide or iodide ions.

Figure 7B:
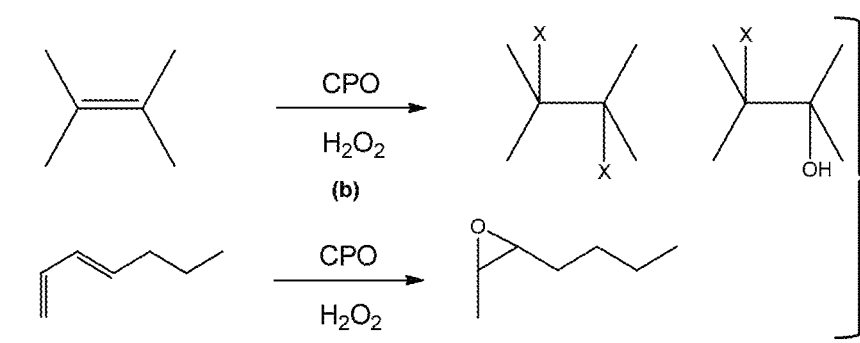
Figure 7C:
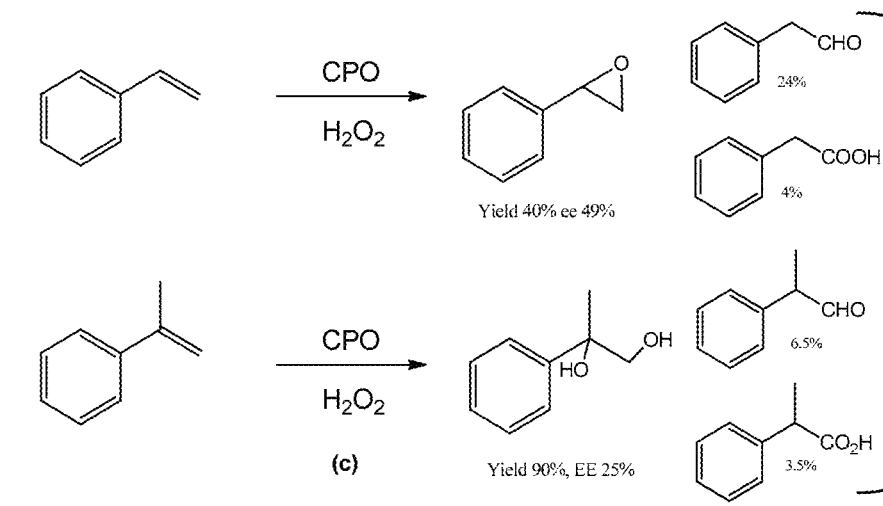
Figure 8:
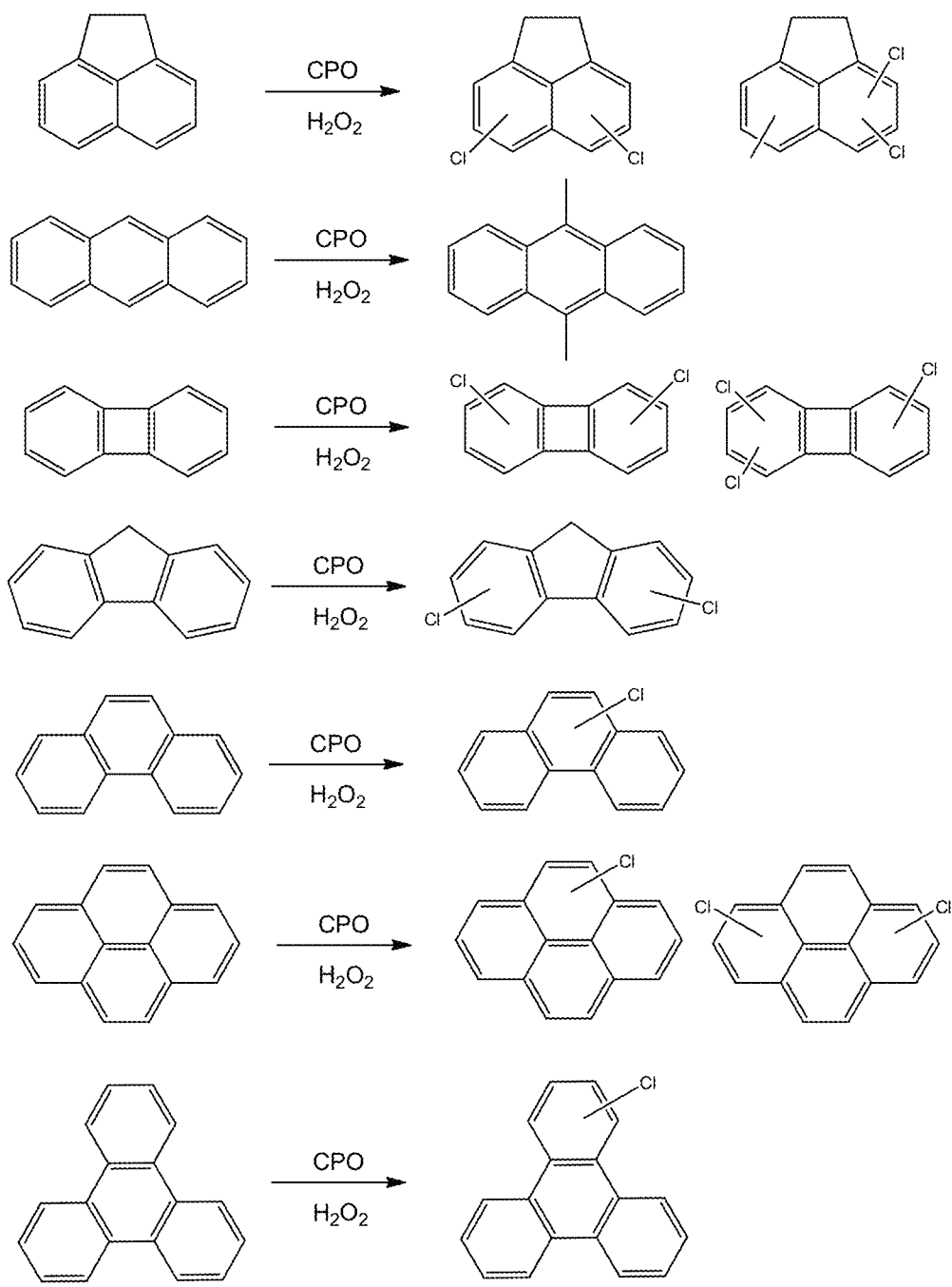
FIG. 8 shows CPO-catalyzed chlorination of aromatic substrates in phosphate buffer with chloride ions.

FIG. 8 shows that halogenation of other substrates can be catalyzed by CPO, such as phenols and, as FIG. 7B shows, 1,3-cyclopentanedione and alkenes. The oxidative chlorination catalyzed by CPO for halogenated phenols or phenols typically generates different isomers. FIG. 7C shows other important two-electron oxidations, including epoxidation with enantioselectivity and hydroxylation.

Mechanism of CPO-Catalyzed Reactions

Figure 9:
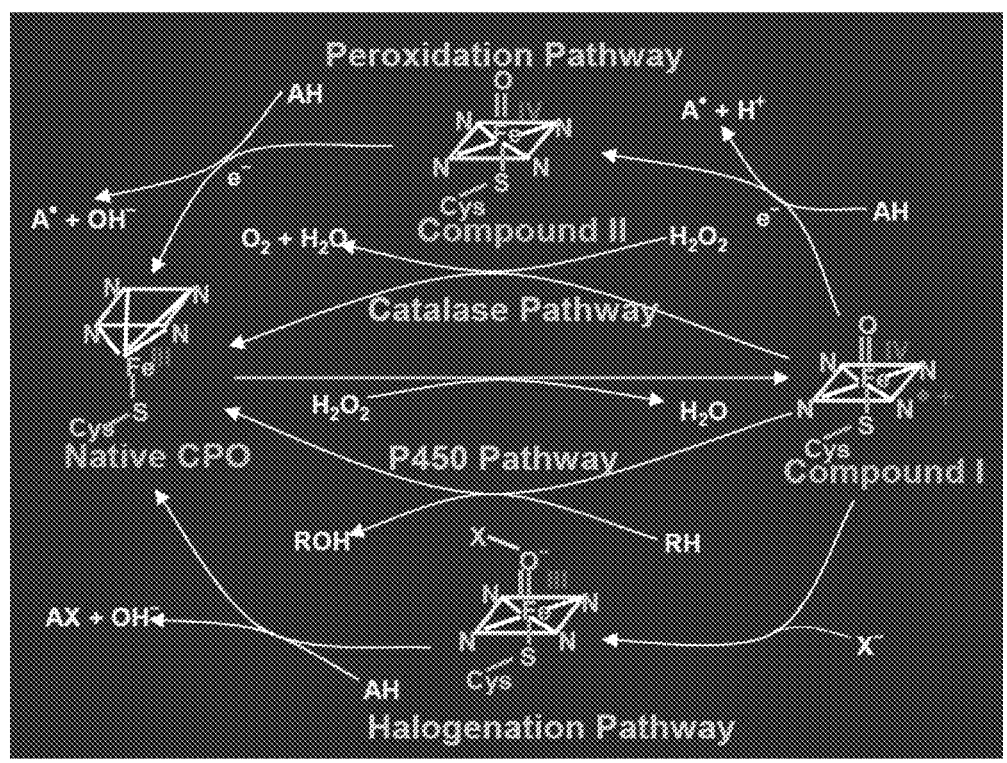
FIG. 9 shows the general mechanism of a CPO-catalyzed reaction. AH represents the substrate. Compounds I and II represent the ferryl intermediates. X represents halogen atoms (except $F^-$).

FIG. 9 shows the general catalytic cycle of CPO, starting from the resting state of the enzyme. The native ferric center binds with $H_2O_2$ at the heme iron to form an oxo-ferryl cation radical intermediate, Compound I. During the reaction, two electrons from the heme center are transferred to $H_2O_2$, cleaving the O—O bond and producing $H_2O$.

Compound I is involved in multiple reaction pathways. In the "dismutation" or "catalase" pathway, Compound I continues to react with $H_2O_2$ to generate $O_2$ and $H_2O$ and is reduced back to its resting state. In the "P450" pathway, an organic substrate (RH) is hydroxylated and Compound I is reduced back to its ferric resting state.

In the "peroxidation" pathway, another reactive oxo-ferryl intermediate, Compound II, is formed. One electron from Compound I is transferred to an organic molecule (AH), converting AH to a radical molecule (A.). The electron is transferred to the organic substrate from Compound II, and CPO is returned to its resting state.

In the "halogenation" pathway, Compound I interacts with a halide (X) to form Compound X, a ferric intermediate. Compound X will halogenate an organic substrate (AH) and generate a hydroxyl ion ($OH^-$). It then returns back to its resting state.

Compound I, with its strong oxidizing capabilities, also generates hypochlorous acid and/or hypobromous acid as active intermediates in oxidative chlorination.

Selected Definitions

As used herein, a "remedially-effective amount" of the composition or any component of the composition is any amount or concentration that will result in the treatment or remediation of polluted or contaminated wastewater or other water sources.

As used herein, "treatment" or "remediation" of wastewater or other water sources refers to the act or process of, or the result of, correcting a fault or deficiency, such as in modulating, ameliorating, reducing, reversing, or stopping damage or harm to the health of humans, other organisms, or the environment. This is achieved by acting upon contaminants in the environment, such as hazardous or polluting materials, which may be changed chemically, or physically, or degraded, stabilized or sequestered, or in some other way removed from the surrounding environment. Treatment may comprise degradation and/or reduction of pollutants in water and can include the use of the compositions of the present invention, either alone or in combination with other known treatment methods, including but not limited to UV treatment, activated sludge, and bioremediation.

As used herein, "degradation" of a chemical compound can be used interchangeably with "dissolution," "decomposition" and "digestion," and refers to the breakdown or separation of the compound into two or more simpler products. The products resulting from degradation of a chemical compound can be, for example, simpler compounds, metabolites, or elemental parts.

As used herein, "bioremediation," means using biological organisms, alone or in conjunction with inert structures, as a system for treating, modulating or altering the contaminants, such as hazardous or polluting materials.

As used interchangeably herein, "contaminant" or "pollutant" means any molecule, chemical or organism in the environment that is harmful to other living organisms in the environment or to the abiotic elements of the environment, and includes compounds or molecules that are in an amount greater than is desired for that environment even if such compounds or molecules are not inherently harmful if found in lower amounts. Biological, chemical, physical, or radiological substances (normally absent in the environment) which, in sufficient concentration, can adversely affect living organisms through air, water, soil, and/or food are included in the terms "contaminant" or "pollutant." The term, "toxic materials" as used herein, is included in the term "contaminant." Pollutants may also be a natural element of the environment that is present in such a concentration that it is now harmful to the environment and its constituents. The pollutant may be an element that has been introduced into the environment by human or animal activities, such as synthesis of the material, or by natural causes.

Contaminant or pollutant, as used herein, also means any molecules, chemicals or organisms in the environment that are present in an undesired concentration or amount. The contaminant may not necessarily be harming any component of the environment but may be present in an undesired quantity.

Contaminant or pollutant, as used herein, also encompasses the phrases "pharmaceutical pollutant" and "environmentally persistent pharmaceutical pollutant (EPPP)," which refer to any compound specifically designed and/or produced for use by humans or animals as a medicinal drug or for personal care, which is obtained either by prescription or OTC, and which has entered, persisted, and/or disseminated in the environment. Non-limiting examples of pharmaceutical pollutants include compounds from the following classes of drugs: acetaminophen, amoxicillin, azithromycin, bacitracin, ciprofloxacin hydrochloride, doxycycline, erythromycin, lincomycin, naproxen, penicillin G, penicillin V, sulfadiazine, sulfamethazine, sulfamethizole, sulfamethoxazole, tetracycline, trimethoprim, diclofenac, carbamazepine, atenolol, bezafibrate, lidocaine, clarithromycin, diatrizoate, iopamidol, iopromide, cyclophosphamide, and ifosfamide.

The term, "environment" as used herein, is defined generally as the site, surroundings or conditions in which a person, animal, or plant lives or operates, and more specifically in terms of remediation, as an area as defined by the contaminant/pollutant situation. Environment may include the biotic and abiotic elements, and the patterns of the interrelationships between the biotic elements, and between the biotic and abiotic elements that are found in the defined area. All three physical states (solids, liquids, and gases) may be included in the elements that make up the environment.

The term environment also encompasses the phrases "wastewater" and "water source." Wastewater refers to any water, the quality of which has been adversely affected by human or animal activities. Such activities can include domestic, industrial, commercial, or agricultural activities. Further included in the term wastewater are surface runoff, or storm water, and municipal wastewater, or sewage. A water source is any body of water in the environment, either naturally occurring or man-made, including groundwater, aquifers, rivers, streams, lakes, ponds, and the like. Water sources can include but are not limited to water used for drinking, recreation, or habitation.

As used herein, the terms "isolated," and "purified," refer to material that is substantially or essentially free from components that normally accompany the compound as found in its native state. Purity and homogeneity are typically determined using analytical chemistry techniques. Particularly, in preferred embodiments, the compound is at least 85% pure, more preferably at least 90% pure, more preferably at least 95% pure, and most preferably at least 99% pure.

Compositions of the Subject Invention

One embodiment of the subject invention provides a composition for treating wastewater or another source of water comprising remedially-effective amounts of the enzyme chloroperoxidase, an oxidant, and a halogen ion, wherein the remedially-effective amounts are combined to form a system capable of degrading pollutants present in the wastewater or water source. Any reference to a "CPO—$H_2O_2$—$X^-$ system", where X is a halide, is intended as a reference to a composition according to the subject invention.

In preferred embodiments, the concentration of hydrogen peroxide and CPO, as well as the pH level of the composition of the subject invention, are optimized based on the actual substrate being treated with the composition.

In some embodiments, chloroperoxidase is in its pure form. The growth medium of *Caldariomyces fumago* functions similarly to the pure form of CPO. In other embodiments, chloroperoxidase is used in a crude protein form.

In some embodiments, isolated CPO is present in the composition in a remedially-effective amount. CPO concentration preferably ranges from about 0.1 nM to about 50 nM. In a specific embodiment, when, e.g., diclofenac is the substrate being treated, CPO is present at a range from about 0.25 nM to about 6.0 nM, preferably at a concentration above 5.0 nM. In another embodiment, when, e.g., naproxen is the substrate being treated, CPO is present at a range from about 1.0 to about 23.0 nM, preferably at a concentration above 20.0 nM. In yet another embodiment, when, e.g., APAP, CBZ, or SMZ is the substrate being treated, CPO is present at a range from about 0.4 nM to about 5.0 nM.

In another embodiment, the oxidant of the claimed composition is a hydroperoxide. In specific embodiments, the oxidant is hydrogen peroxide ($H_2O_2$). Preferably, hydrogen peroxide is present in the composition in an amount below that which causes degradation of CPO. It is well known that high concentration of $H_2O_2$ (an oxidant) inactivates most heme containing enzymes due to internal oxidative destruction of the porphyrin prosthetic group. Thus, low concentrations of $H_2O_2$ are employed for reactions catalyzed by most heme peroxidases. However, this strategy cannot be simply applied to CPO because of its ability to catalyze the disproportionation (i.e., a redox reaction producing two different products from the oxidation and reduction of the same element) of hydrogen peroxide. Therefore, optimum concentration of hydrogen peroxide depends on the actual substrate being degraded, and includes the amount of substrate that is being degraded.

In specific embodiments of the present invention, hydrogen peroxide is present in the composition at a concentration from about 0.03 mM to about 2.0 mM, more preferably from about 0.1 mM to about 0.7 mM, and even more preferably from about 0.3 mM to about 0.5 mM.

Hydrogen peroxide concentration can also be determined with respect to the amount of substrate being treated. For example, in certain embodiments, the ratio of concentration of substrate to hydrogen peroxide is 7:1, 6:1, 5:1, 4:1, 3:1, or 2:1.

In another embodiment, the composition further comprises a remedially-effective amount of a halogen ion. The halogen ion can be selected from chloride, bromide, and iodide. In another embodiment, the halogen ion is obtained by the addition of a remedially-effective amount of halide salt, such as potassium chloride or potassium bromide. The halogen ion can be present at, for example, a concentration ranging from about 0.01 mM to about 50 mM, preferably from about 0.05 to about 30 mM, more preferably from about 5.0 mM to about 25 mM, even more preferably from about 15 mM to about 20 mM.

In another embodiment, the CPO is conjugated to poly [hydroxyethyl methacrylate-co-(poly(ethylene glycol)-methacrylate] membranes to stabilize the CPO and increase the recyclability of the enzyme. This can enhance the storage and thermal stability of CPO versus that of free CPO.

Use of the Composition for Water Treatment

The composition of the subject invention can be used to catalyze degradation of pollutants in wastewater or other water sources. In specific embodiments, the pollutant is a pharmaceutical pollutant.

In particular embodiments, the pharmaceutical pollutant is from one of the following classes of drugs: acetaminophen, carbamazepine, sulfamethazine, diclofenac, and naproxen. These pharmaceuticals are commonly used in human and veterinary medicine and persist in the environment.

Another embodiment provides methods for treating wastewater or other polluted water sources comprising administering a remedially-effective amount of the composition to the wastewater or water source; allowing the composition to catalyze degradation of pollutants within the water source; and allowing the water pollutants to sufficiently degrade.

In a particular embodiment, sufficient degradation is achieved when treatment or remediation of the water has occurred. In another embodiment, sufficient degradation can be total degradation of water pollutants.

The rate of degradation can vary depending on certain factors, such as the drug compound being treated and the concentration of oxidant and/or CPO applied. In certain embodiments, sufficient degradation occurs in less than 1 minute. In other embodiments, the sufficient degradation takes from about 1 minute up to about 5 minutes, to about 10 minutes, to about 1 hour, to about 24 hours, or longer.

The claimed method can be carried out at relatively low pH. In specific embodiments, the present method is carried out within a pH range of about 2.0 to about 5.0, preferably within the range of about 2.5 to about 3.5, and even more preferably within the range of about 2.75 to about 3.2.

In certain embodiments, the method can be carried out in combination with other wastewater treatment methods. Metabolites and/or products of drug compounds can be susceptible to removal via biological treatments, activated sludge, or UV treatment, for example. Thus, products can be removed using these secondary treatment processes, providing even greater degradation efficiency for water pollutants.

In another embodiment, exemplified below, methods are provided for identifying the metabolites of acetaminophen (APAP), carbamazepine (CBZ), and/or sulfamethazine (SMZ). Another embodiment provides methods for identifying the products of CPO-catalyzed degradation of diclofenac and naproxen. Further embodiments provide methods for determining the degradation pathways of APAP, CBZ, SMZ, diclofenac, and naproxen.

In another embodiment, the method further comprises the step of testing the wastewater or water source in which the composition of the subject invention is administered for the presence of known drug metabolites and/or products after degradation has occurred.

The examples described below illustrate exemplary embodiments of the materials and methods of the subject invention. These exemplary embodiments should not be construed as limiting the scope of the subject invention.

Example 1—CPO-Catalyzed Chlorination and Polymerization of Acetaminophen

Acetaminophen

Acetaminophen (N-acetyl-p-aminophenol, APAP), also known as paracetamol, is an active ingredient in many OTC medications. It is widely used as a pain reliever and fever reducer.

The following experiments provide investigations into the efficiency of CPO-catalyzed degradation of APAP, while also proposing the degradation pathway and metabolites of APAP. As noted previously, CPO contains an analogous proximal heme iron thiolate ligand structure to that of P450, but for degradation of APAP, the CPO—$H_2O_2$—$Cl^-$ system works differently from a P450-hypochlorite system. Mainly, chlorination and dimerization are preferred over oxidation, suggesting CPO possesses special capabilities for detoxification of APAP.

Experimental Materials and Methods

The isolation of CPO proposed in this study was a modification of the protocol reported by Morris and Hager (1966), using acetone instead of ethanol as the fractionation solvent. CPO with Rz=1.45 was applied in all reactions (Rz is the purity standard, defined as A398/A280=1.44 for a pure enzyme). All solvents were HPLC grade or Optima® LC/MS grade, purchased from Thermo Fisher Scientific Inc. (Waltham, Mass., USA). Water was produced using a Milli-Q® Biocel™ Ultra-Pure water purification system equipped with 0.22 µM membrane filter cartridge (EMD Millipore, Billerica, Mass., USA), and an organic removal cartridge (Evoqua Water Technologies, Lowell, Mass., USA).

UV-Visible Spectrophotometry

A VARIAN UV-Vis spectrophotometer (Cary 200 Bio) was used to collect the UV spectra of the degradation products. The drug solution was scanned by dissolving 0.11 mM APAP in 100 mM $KH_2PO_4$ buffer with 20 mM KCl at pH 2.75. The same solution was monitored after being mixed with 0.55 mM $H_2O_2$. The reaction was initiated with the addition of 5 nM CPO and the UV-Vis spectrum was recorded for reaction times of 1 min., 2.5 min., and 4 min.

Liquid Chromatography and Mass Spectrometry

To investigate the degradation efficiency, 62.56 µM APAP was reacted with 321.56 µM $H_2O_2$ and 0.43 nM CPO for 1 hour at room temperature. The mixture was centrifuged at 3,000 g in Centriprep® centrifugal filter unit with a 30,000 Dalton cut-off membrane (EMD Millipore, Billerica, Mass., USA). The yielded product was collected after being centrifuged for 1 min. Ethyl acetate was used to extract the filtrate while shaking vigorously, and the supernatant was evaporated to dryness using nitrogen gas. The dried metabolites were dissolved in $H_2O$/methanol (95:5 v/v) to achieve a final concentration of 1 mg/L (ppm). Each sample was either stored in a freezer at −20° C. or immediately run in the LC-Q-TOF-MS mass spectrometer system.

A low concentration of CPO and $H_2O_2$ reaction sample was prepared as follows: 6.86 µM $H_2O_2$ was added directly to Centriprep® centrifugal filter unit with the same membrane size as described above. Then, 66.20 µM APAP was added, catalyzed by the addition of 1.28 nM CPO in 100 mM phosphate buffer with 20 mM KCl for 3 min. and 5 min. The experiments were run in triplicate. Dried metabolites were dissolved in $H_2O$/methanol (95:5 v/v) to achieve a concentration of ~1 mg/L (ppm) and analyzed by the LC-Q-TOF-MS system immediately.

Next, a high concentration of APAP sample was prepared by mixing 413 µM APAP with 2 mM $H_2O_2$, catalyzed by 2 nM CPO for 35 min. at room temperature. The extraction was carried out by ethyl acetate, and the organic layer was dried using nitrogen gas. Metabolites were dissolved in 1.5 mL $H_2O$/methanol (95:5 v/v) to achieve an approximate final concentration of 5 mg/L (ppm). The sample was filtrated through a 0.22 µM polyethersulfone syringe filter. The sample was stored in a freezer at −20° C. and analyzed using both a Q-TOF-LC-MS and Triple-quadrupole LC-MS/MS system.

Instrumentation and Chromatographic Separation

Chromatographic separation and identification of metabolites was performed using the Agilent 1290 Infinity UPLC system coupled with Agilent 6530 Q-TOF mass spectrometer. The Agilent MassHunter Data Acquisition Software (rev. B0.06.00) was used to control the UPLC and the mass spectrometer. Mass Hunter Qualitative Data Analysis Software (Rev. B.07.00) was used for data mining and identification. An Agilent ZORBAX Eclipse plus C18 Rapid Resolution High Definition (RRHD) column (100 mm×1.8 µm) was applied, with the column temperature set at 30° C. via a thermostatted column compartment (TCC). An infinity 1290 automatic injector was used to inject 1 µL of the sample to the column. A flow rate of 0.4 mL/min was used with an aqueous mobile phase A, consisting of water with 5 mM ammonium formate and 0.1% formic acid, and an organic mobile phase B, consisting of acetonitrile with 0.1% formic acid. The optimized chromatographic gradient was at 0 minutes, 95% A, and 5% B. B increased linearly to 95% over 8 min. and this gradient was maintained for 1 min. The positive ionization mode was applied during all experiments.

In full scan MS mode, the accurate mass data of the molecular ions were processed through the Agilent MassHunter Qualitative Analysis software. The collected retention times and confirmed formulas of every metabolite were applied in targeted MS/MS mode to identify metabolite information.

Additionally, an Agilent 6460 Triple-Quadrupole LC/MS/MS mass spectrometer was used to increase the detection sensitivity of the isolated metabolites that were initially identified by the LC-QTOF mass spectrometer. The same column and elution program previously used in the LC-QTOF was employed in the LC-QQQ-MS system.

Results

UV-Vis Study of CPO-Catalyzed Degradation of APAP

Figure 10:
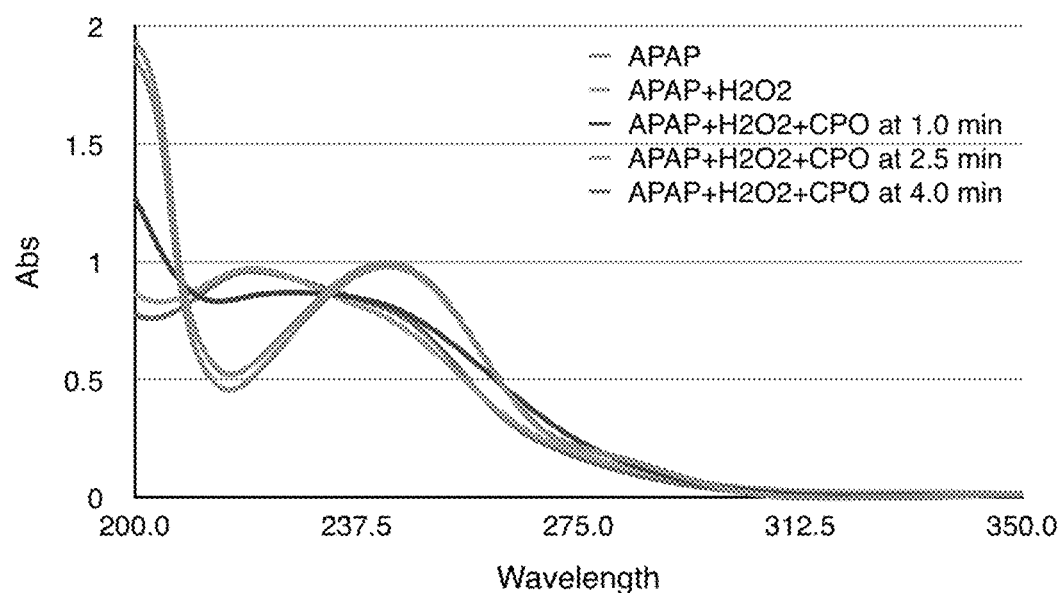
FIG. 10 shows a graphical representation of the UV-Visible (UV-Vis) spectra of CPO-catalyzed degradation of N-acetyl-p-aminophenol/Acetaminophen (APAP), APAP with $H_2O_2$, and APAP metabolites at 1 min, 2.5 min, and 4 min.

The UV-Vis spectra of APAP (0.11 mM) were scanned in 100 mM $KH_2PO_4$ buffer with 20 mM KCl at pH 2.75. FIG. 10 shows the spectra of APAP with $H_2O_2$ and its metabolites. APAP showed a strong absorption at 242 nm. After mixing with 0.55 mM $H_2O_2$, the absorption curve increased slightly due to absorbance of $H_2O_2$. One minute after addition of 5 nM CPO, the 477 nm absorption decreased, then increased at 4 minutes Absorption at 218 nm increased after 1 minute, and stopped increasing at 2.5 minutes.

The same reaction was carried out under the same conditions, but without the chloride ion (KCl) in the phosphate buffer. Without KCl, the absorbance did not change after the addition of CPO, meaning the $Cl^-$ is necessary in the degradation of APAP in the CPO—$H_2O_2$—$Cl^-$ system.

Degradation Efficiency—LC-Q-TOF-MS 62.56 µM APAP was reacted with $H_2O_2$ (321.56 µM) and CPO (0.43 nM) for 1 hour. The sample was analyzed by LC-Q-TOF-MS. APAP was not observed, meaning degradation efficiency of 100% was achieved.

Seven (7) APAP metabolites (coded AM1 to AM7) were confirmed by different retention times and accurate mass-to-charge ratios (m/z). FIG. 11 shows the elemental formula, retention time, relative mass difference between observed mass and mass of the target compound (ppm), and difference between the observed mass and mass of the target compound (in milliDaltons) for each metabolite.

Figure 12:
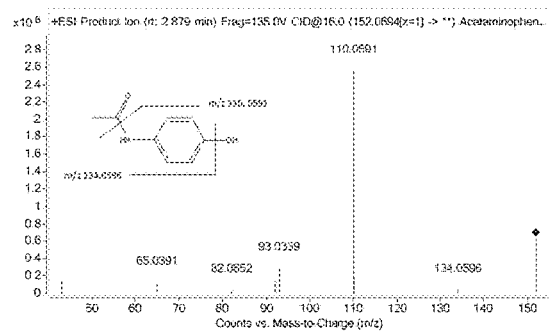
FIG. 12 shows the targeted MS/MS spectra of APAP and its metabolites.
Figure 12:
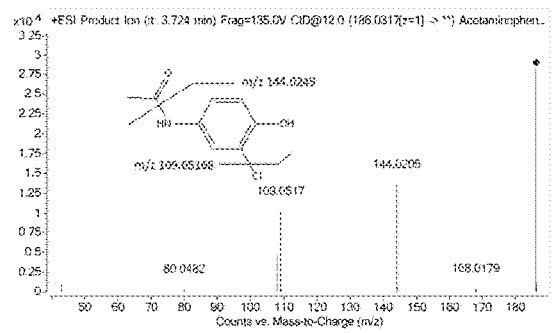
Figure 12:
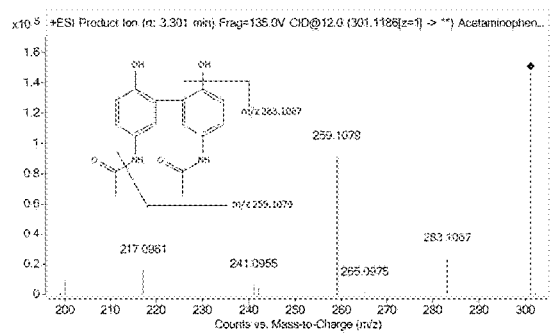
Figure 12:
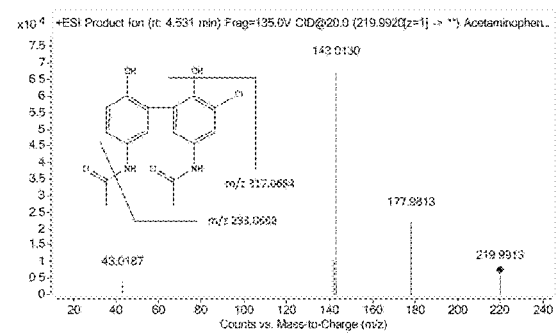
Figure 12:
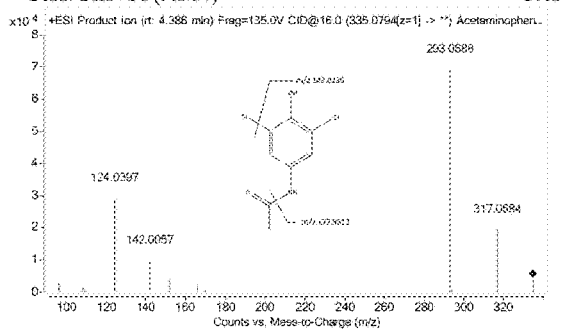
Figure 12:
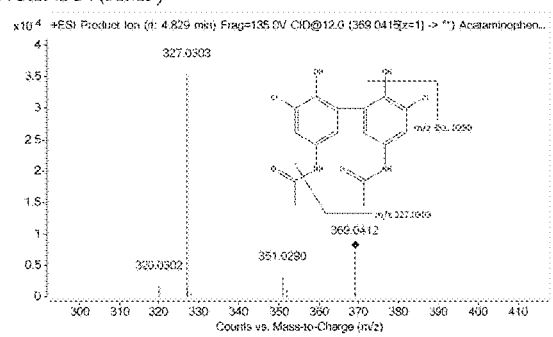
Figure 12:
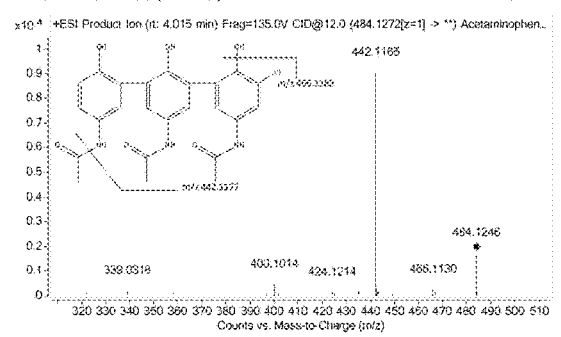
Figure 12:
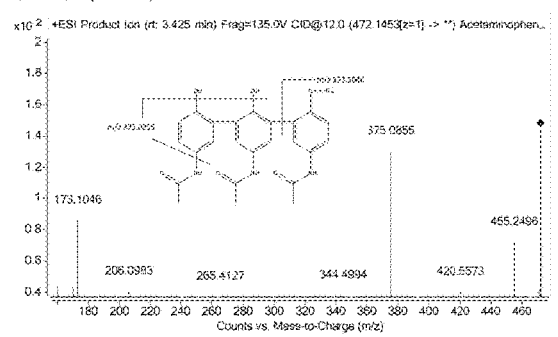

The structures of each metabolite were confirmed in targeted MS/MS by retention time and fragment ions. FIG. 12 shows the targeted MS/MS spectra of APAP and its metabolites.

Discussion

When APAP mixes with hypochlorite, toxic products such as 1,4-benzoquinone and N-acetyl-p-benzoquinone imine (NAPQI) have been reported. These products were not detected in the CPO—$H_2O_2$—$Cl^-$ system. Rather, evaluation of the toxicity of the final products indicated that CPO resulted in excellent purification of the wastewater when compared with commonly used chlorine disinfection systems.

Example 2—CPO-Catalyzed Degradation of Carbamazepine

Carbamazepine (CBZ) is widely used in the treatment of epilepsy, trigeminal neuralgia and bipolar disorder. CBZ is detectable in surface water, ground water, and even drinking water. Various harmful ecological effects, for example in fish and rodents, suggest the possibility that long term exposure to CBZ in drinking water is also a potential risk to human health.

Degradation efficiency in water, kinetic parameters, degradation pathways, and the products of CPO-catalyzed degradation of CBZ were investigated in this experiment under optimized conditions, including concentrations of Cl- and $H_2O_2$, and pH.

UV-Visible Spectrophotometry

A VARIAN UV-Vis spectrophotometer (Cary 200 Bio) was used to collect the UV spectra of the degradation products. The drug solution was scanned by dissolving 0.07 mM CBZ in 100 mM $KH_2PO_4$ buffer with 20 mM KCl at pH 2.75. The same solution was monitored after being mixed with 0.35 mM $H_2O_2$. UV spectra were recorded after the addition of 5 nM CPO for 1 min., 2.5 min., and 4 min.

The effect of the concentration of chloride was investigated. Degradation was carried out in 100 mM phosphate buffer at pH 3.0 with 0.07 mM CBZ and 0.07 mM $H_2O_2$. Concentration of chloride was increased from 0 to 20 mM. 285 nm wavelength was monitored immediately after 2.5 nM CPO was added.

The degradation rate at pH range of 2.0 to 5.0 was investigated to probe the effect of pH on the CPO-catalyzed reaction. The reaction was carried out in 100 mM phosphate buffer with 20 mM KCl, 0.07 mM CBZ, and 0.07 mM $H_2O_2$. $H_3PO_4$ and KOH were used to adjust pH. 285 nm wavelength was monitored immediately after the addition of 2.5 nM CPO. The calculated time was 0.2 to 0.4 min.

The degradation rate of CBZ was determined by different concentrations of $H_2O_2$, ranging from 0.07 to 0.71 mM, in 100 mM phosphate buffer with 20 mM KCl and 0.07 mM CBZ at pH 3.0. A wavelength of 285 nm was monitored immediately after the addition of 5 nM CPO. The degradation rate was calculated at 0.1 to 0.3 min.

The rate was calculated by monitoring absorbance at 285 nm from 0.1 to 0.2 min. The reaction was carried out in 100 mM $KH_2PO_4$ buffer with 20 mM KCl at pH 2.75, with the concentration of CBZ varying from 0.02 to 0.11 mM. UV monitoring was started immediately after adding 0.35 mM $H_2O_2$.

All experiments were triplicated and data reported were mean values of three independent measurements with standard deviation.

Liquid Chromatography and Mass Spectroscopy

To investigate degradation efficiency, CBZ was dissolved in methanol to make stock solution (21.19 mM). 10.59 μM (2.5 mg/L) CBZ was reacted with 107.19 μM $H_2O_2$ and 2.9 nM CPO for 10 min. at room temperature. The sample was prepared using the same technique as described in Example 1. The sample was stored at −20° C. in a freezer, or immediately run in a LC-Q-TOF-MS mass spectrometer system.

To detect all CBZ metabolites, CBZ was dissolved in methanol to make stock solution (21.19 mM). A high concentration of CBZ sample was prepared by mixing 62.56 μM (14.8 mg/L) CBZ with 0.4 nM CPO. $H_2O_2$ stock solution (41.16 mM) was added to the reaction system at 56.5 μL/minute to bring the final concentration of $H_2O_2$ up to 316.56 μM. The total reaction time was 55 min. The solution was extracted by ethyl acetate, and the supernatant was evaporated by using nitrogen gas. Metabolites were dissolved in 2.0 mL $H_2O$/methanol (95:5 v/v) to achieve a final concentration of ~5 mg/mL (ppm). The sample was centrifuged at 1200 g for 10 min., and 1.5 mL of supernatant was removed by syringe. Filtration was applied using a 0.22 μM polyethersulfone syringe filter. The sample was stored in a freezer at −20° C., and analyzed both using a LC-Q-TOF/MS system and a Triple-Quadrupole LC/MS/MS system.

To investigate the mechanism of degradation, samples were prepared with a low $H_2O_2$ concentration. 6.86 μM $H_2O_2$ was added directly to Centriprep® centrifugal filter unit (30,000 Dalton), along with 42.28 μM CBZ catalyzed by 1.3 nM CPO in the 100 mM phosphate buffer with 20 mM KCl for 1 min., 3 min., and 5 min. Filter units were centrifuged at 3000 g for 1 min. at room temperature. The filtrate was extracted by ethyl acetate, and the organic phase was purged with nitrogen gas to dryness. The dried metabolites were dissolved in $H_2O$/methanol (95:5 v/v) to make the final concentration approximately 1 mg/L (ppm), and immediately analyzed using a LC-Q-TOF-MS system. Experiments were run in duplicate.

The instrumentation and chromatographic separation were the same as that in Example 1.

Results

UV-Vis Study of CPO-Catalyzed Degradation of CBZ

Figure 13:
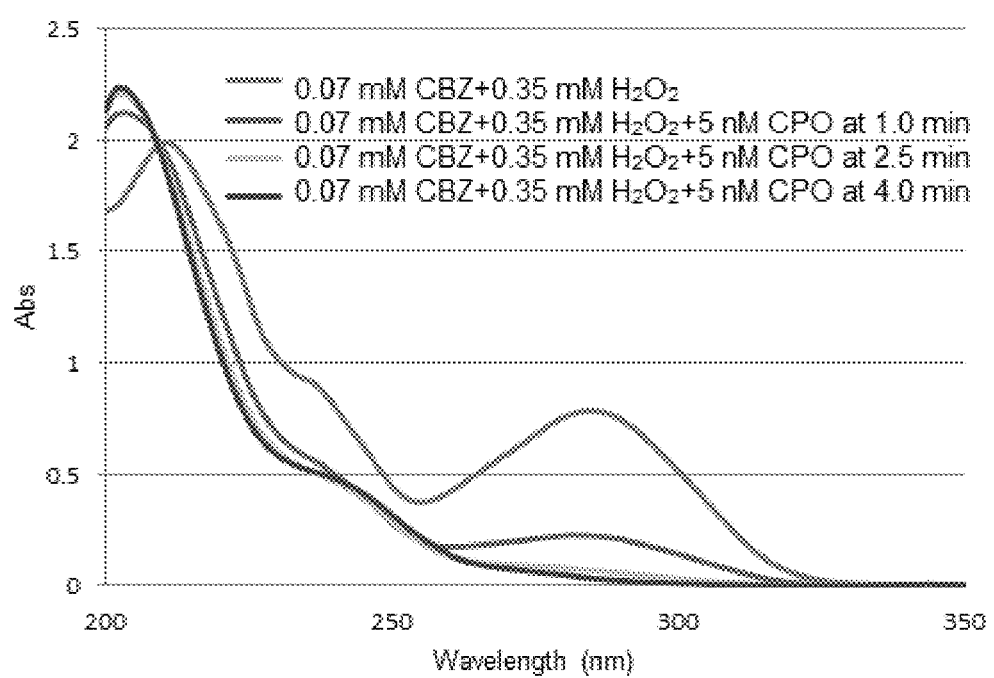
FIG. 13 shows a graph depicting UV-Vis spectra of CPO-catalyzed degradation of carbamazepine (CBZ) with its metabolites and $H_2O_2$ at 1 min., 2.5 min., and 4 min.

FIG. 13 shows UV-Vis spectra of CBZ with $H_2O_2$ and its metabolites at 1 min., 2 min., and 4 min. The spectrum of CBZ showed a strong absorption at 285 nm. 1 min. after addition of 5 nM CPO, the 285 nm absorption decreased, and stopped increasing at 4 min. The 285 nm wavelength was used to measure kinetic parameters of CBZ degradation catalyzed by CPO.

The same reaction was carried out under the same conditions, except for the chlorine ion (KCl) was absent in the phosphate buffer. Without KCl, the absorbance did not change after the addition of CPO. The chlorine ion is necessary in the degradation of CBZ in the CPO—$H_2O_2$—$Cl^-$ system.

The efficiency of degradation catalyzed by 5 nM CPO, calculated by the change of absorbance at 285 nm, was 96% within 4 minutes; however, the efficiency might be more than 96% because the tail of the UV peak of the product appeared to cover the original drug (285 nm).

Figure 14:
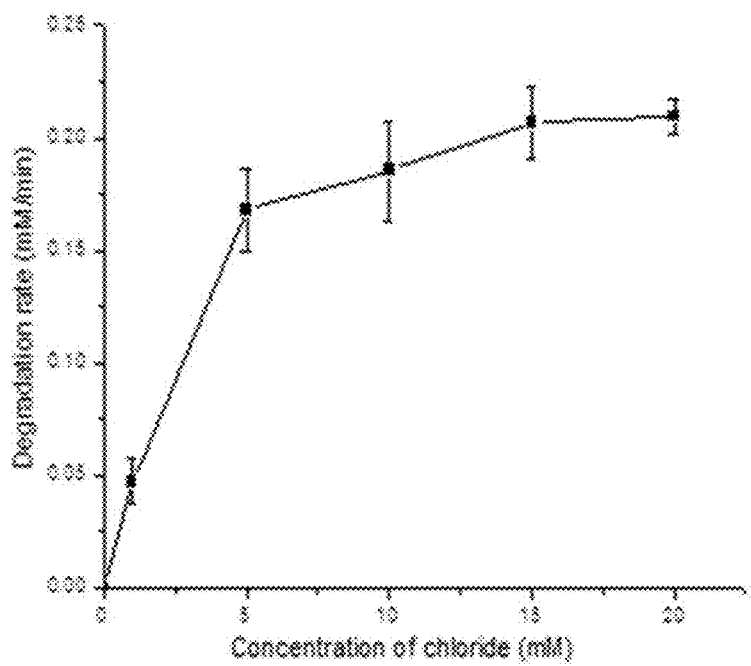
FIG. 14 shows the effect of chloride on the degradation of CBZ.

Effect of Chloride, pH and Hydrogen Peroxide Concentration on the Degradation of CBZ FIG. 14 shows the effect of chloride on the degradation of CBZ. The degradation rate was calculated to range from 0.2 to 0.6 min. The degradation rate increased from 0 to 18.89 M/min. The observation was consistent with those described above, suggesting that chloride participates in the degradation of CBZ.

Figure 15:
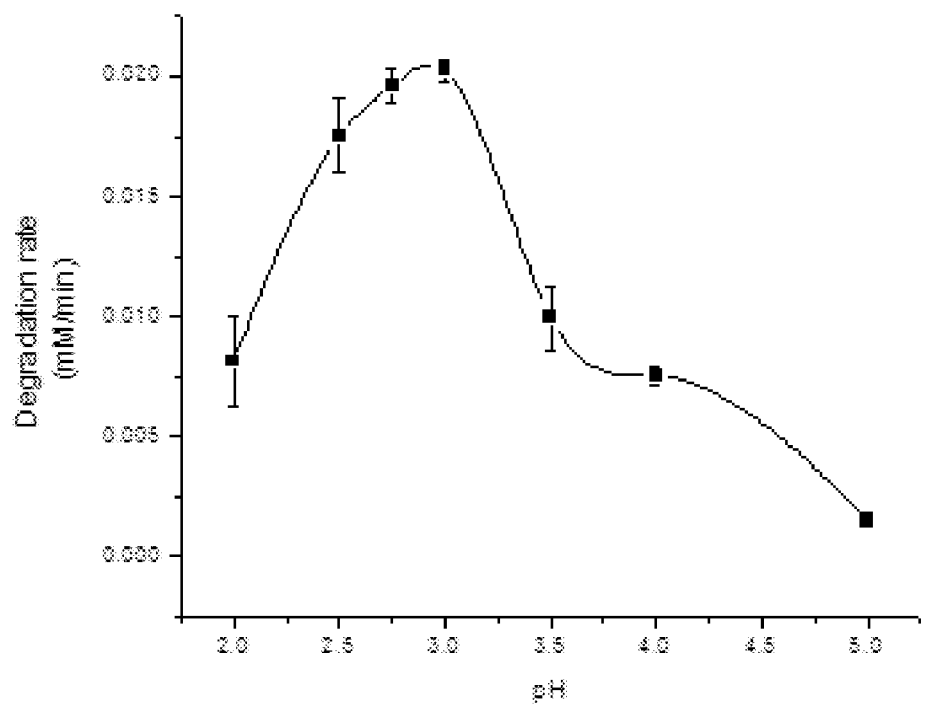
FIG. 15 shows the effect of pH on CBZ degradation.

FIG. 15 shows the effect of pH on CBZ degradation. The optimum pH for the degradation of CBZ is 3.0 in the presence of 20 mM $Cl^-$. The degradation efficiency decreased at a pH of 3.5 to 5. This suggested that CPO could be applied in an acid wastewater treatment.

Figure 16:
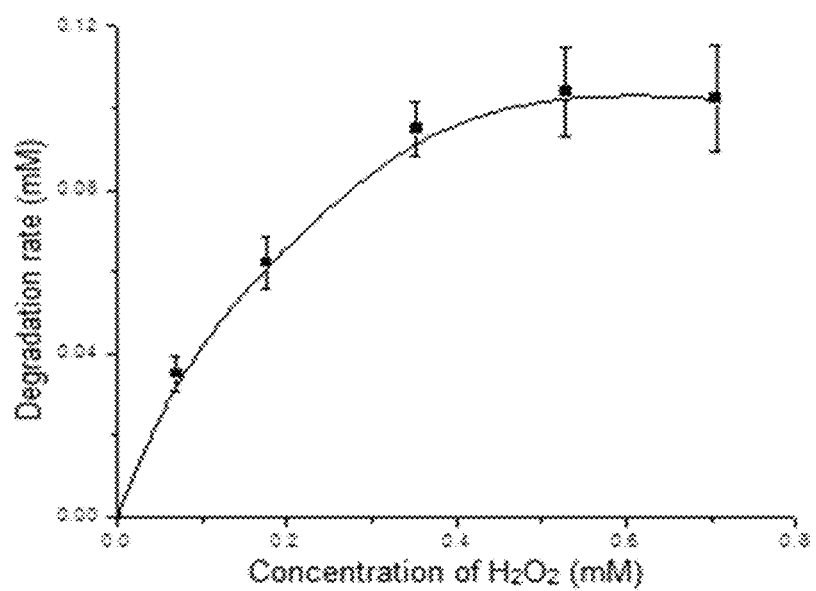
FIG. 16 shows the effect of $H_2O_2$ concentration on degradation rates.

FIG. 16 shows the effect of hydrogen peroxide concentration on degradation. The degradation rate was increased as the concentration of $H_2O_2$ increased to 0.53 mM. From 0.53 to 0.71 mM, the rate was still stable, with only a slight decrease. This could be due to the degradation of CPO by the high concentration of $H_2O_2$. (Manoj, 2010). The stability of CPO in the presence of $H_2O_2$ compared with other peroxidases suggests that CPO has greater prospects for application than others within the same enzyme class.

Figure 17:
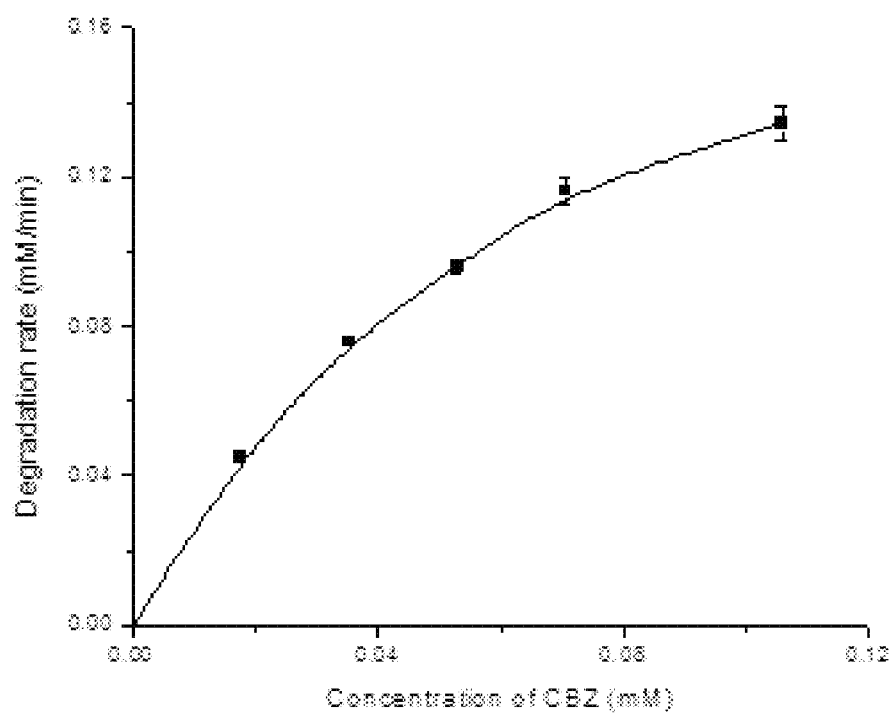
FIG. 17 shows the effect of CBZ concentration on degradation rates.

FIG. 17 shows the effects of different concentrations of CBZ when reacted with 0.07 mM $H_2O_2$ and 5 nM CPO. FIG. 18 shows the calculated kinetic parameters of CBZ degradation catalyzed by CPO.

LC-Q-TOF-MS

To investigate the degradation efficiency of CBZ in the CPO—$H_2O_2$—$Cl^-$ system, CBZ was reacted with $H_2O_2$ and CPO for 10 minutes. The sample was analyzed by LC-Q-TOF-MS, and CBZ was not observed, showing that a degradation efficiency of 100% was achieved even by low concentrations of CPO. This establishes the utility of CPO treatment in large-scale wastewater treatment.

Figure 19:
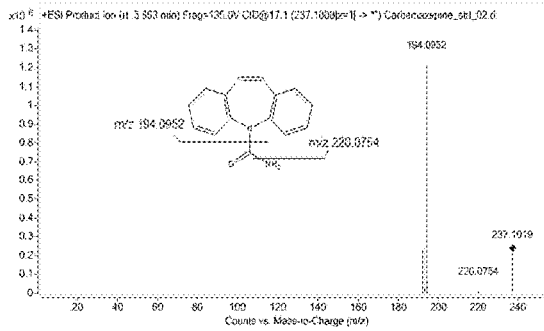
FIG. 19 shows the targeted MS/MS spectra of CBZ and its metabolites.
Figure 19:
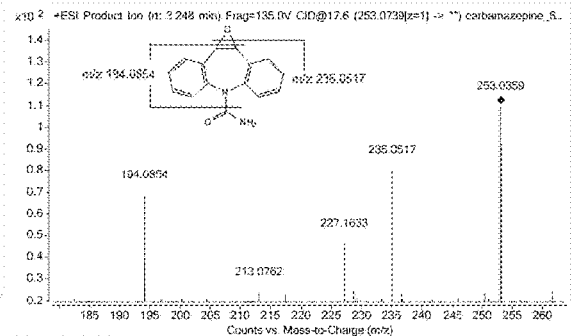
Figure 19:
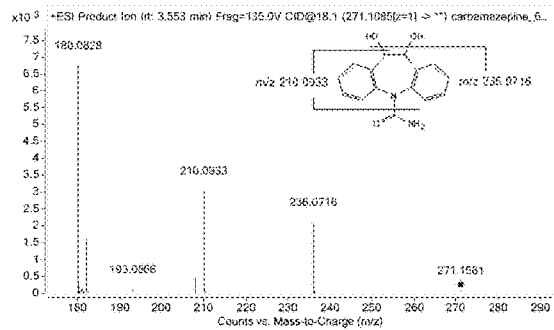
Figure 19:
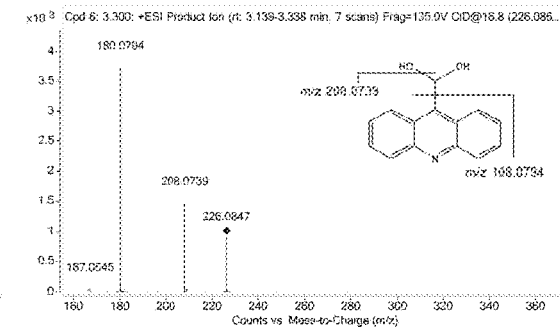
Figure 19:
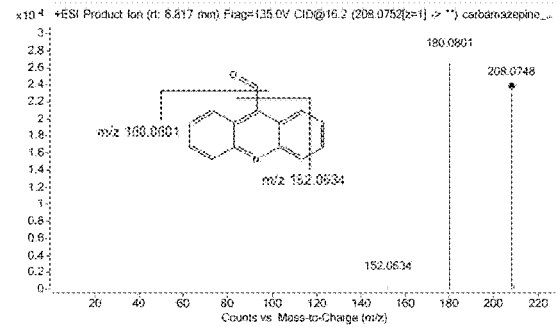
Figure 19:
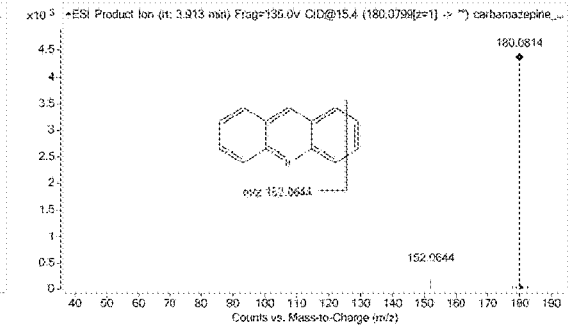
Figure 19:
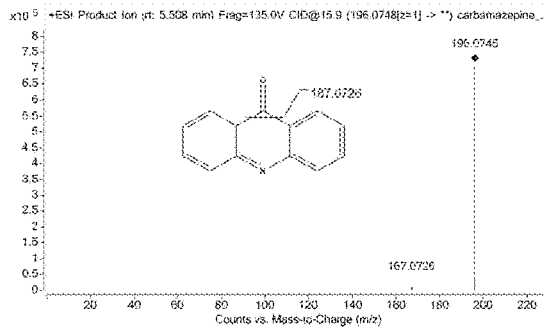
Figure 19:
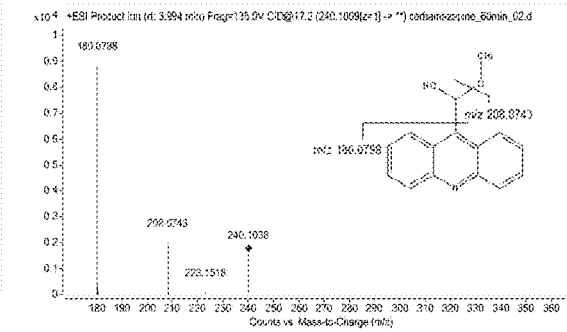
Figure 19:
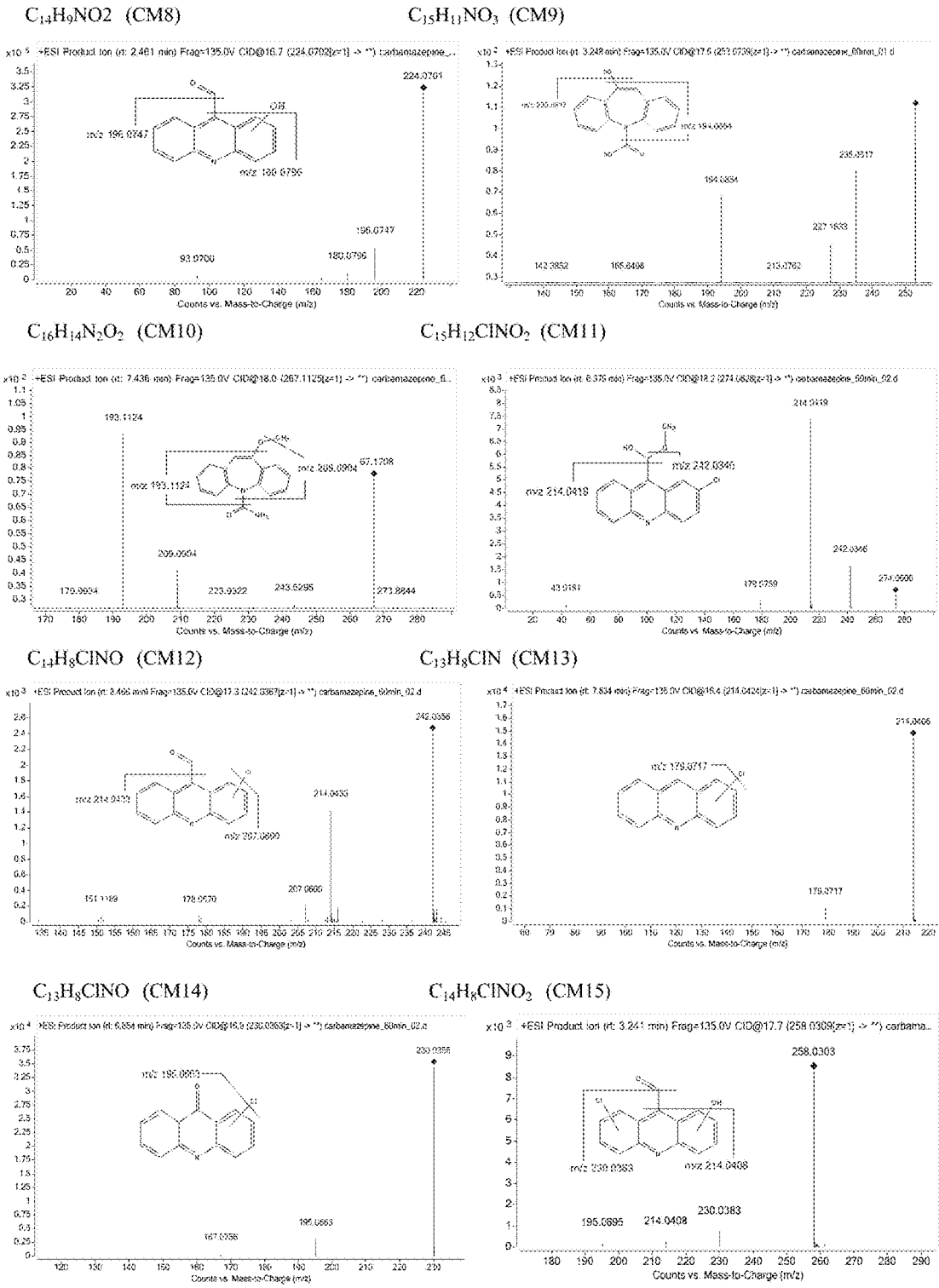

FIG. 19 shows the targeted MS/MS spectra of CBZ and its metabolites. The structures of each metabolite were confirmed by retention time and fragment ions. There were two types of metabolites, distinguished based on their structure. The first type contained CM1, CM2, CM9, CM10, and suggested oxygen insertion into the CBZ-based structure. The other type of structure was based on acridine (CM5), the decarbonylation product of the parent compound. All chlorinated metabolites were from acridine-based structures.

Figure 20:
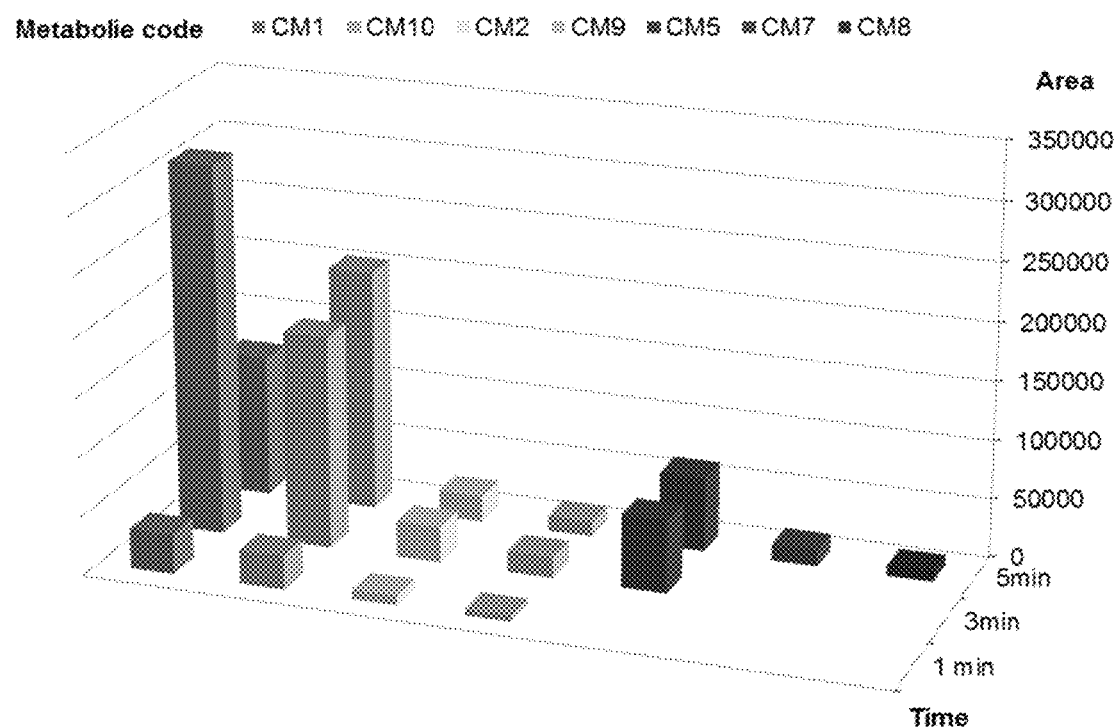
FIG. 20 shows a graph depicting the area of CBZ metabolites with limited $H_2O_2$ at 1 min, 3 min, and 5 min detected by Accurate-Mass LC-Q-TOF-MS.

To investigate the degradation mechanism, this experiment was carried out for a limited reaction time (1, 3, and 5 min.) with low concentration of $H_2O_2$ (6.86 μM). FIG. 20 shows the area of metabolites detected from the reaction. The ratio of the concentrations of CBZ and $H_2O_2$ was about 7:1. Only part of the CBZ was degraded, and only some metabolites were detected, which were potentially the first metabolites formed.

At the first minute, only CM1, CM2, CM9, and CM10 were formed. The four proposed structures were suggestive of oxygen insertion into the CBZ-based structure, produced directly from CBZ without decarbonylation. CM1 was the most abundant metabolite, suggesting that the first step of degradation was the epoxidation of CBZ. The percentage of these four compounds decreased significantly after being reacted with higher concentration of $H_2O_2$ for longer periods of time. At 3 min., acridine (CM5) was formed. CM7 and CM8, two acridine-based metabolites, were detected at 5 min., with final concentrations at relatively high levels.

Compared with the CBZ-based compounds, acridine-based structures appeared to comprise the major products. Acridine (CM5), the decarbonylation product of the parent compound, with CM6, CM7, and CM8 were the most abundant metabolites of the CPO-catalyzed degradation, while CBZ-based structures existed as intermediates of the degradation.

The chlorinated products, CM11-CM15, were observed in relatively low concentrations (together comprising 1.96% of total metabolites). These metabolites were not observed at the first stage of the reaction. Thus, these products were not major products of the CPO-catalyzed degradation reaction.

Figure 21:
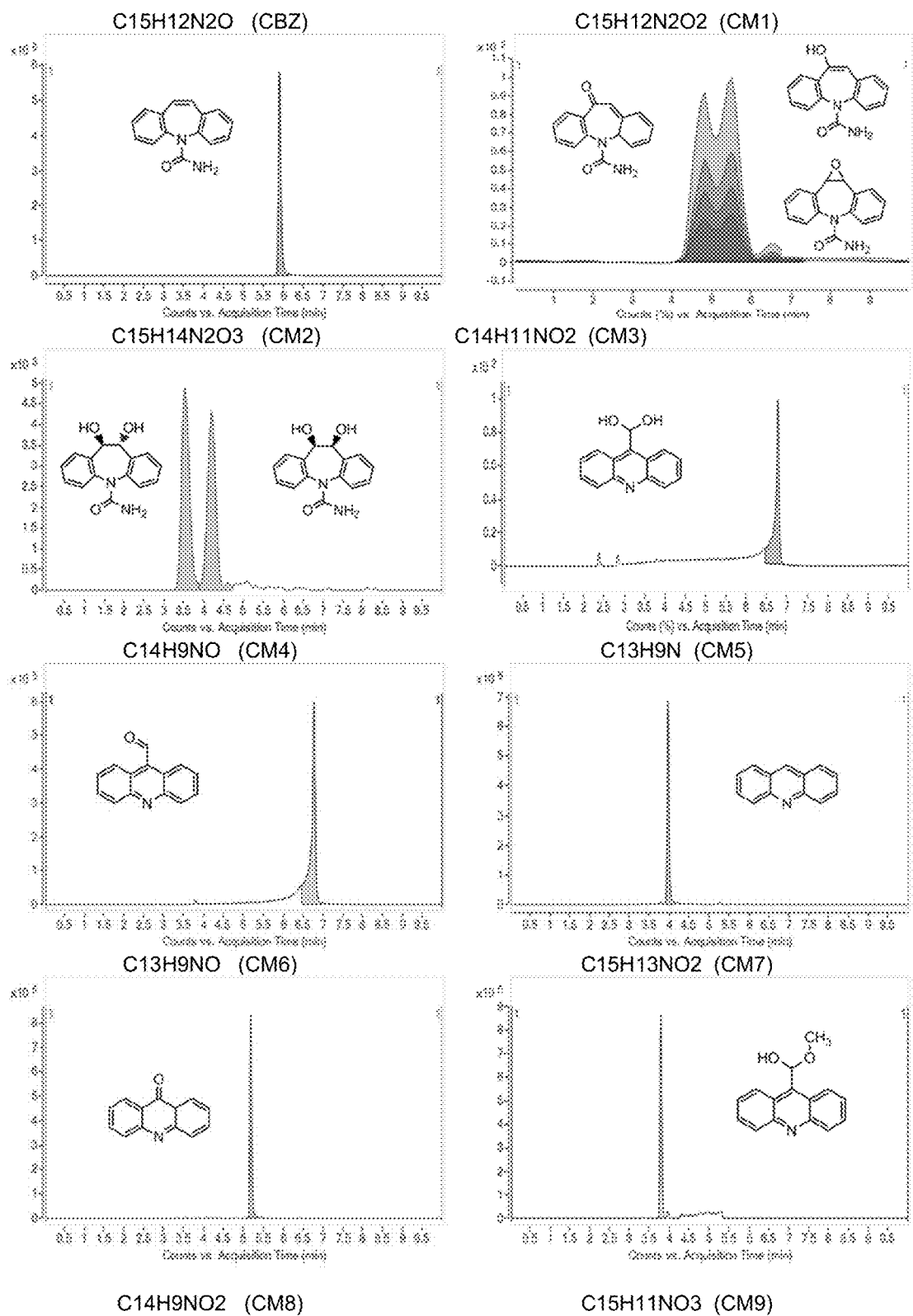
FIG. 21 shows the chromatograms of CBZ and its metabolites.
Figure 21:
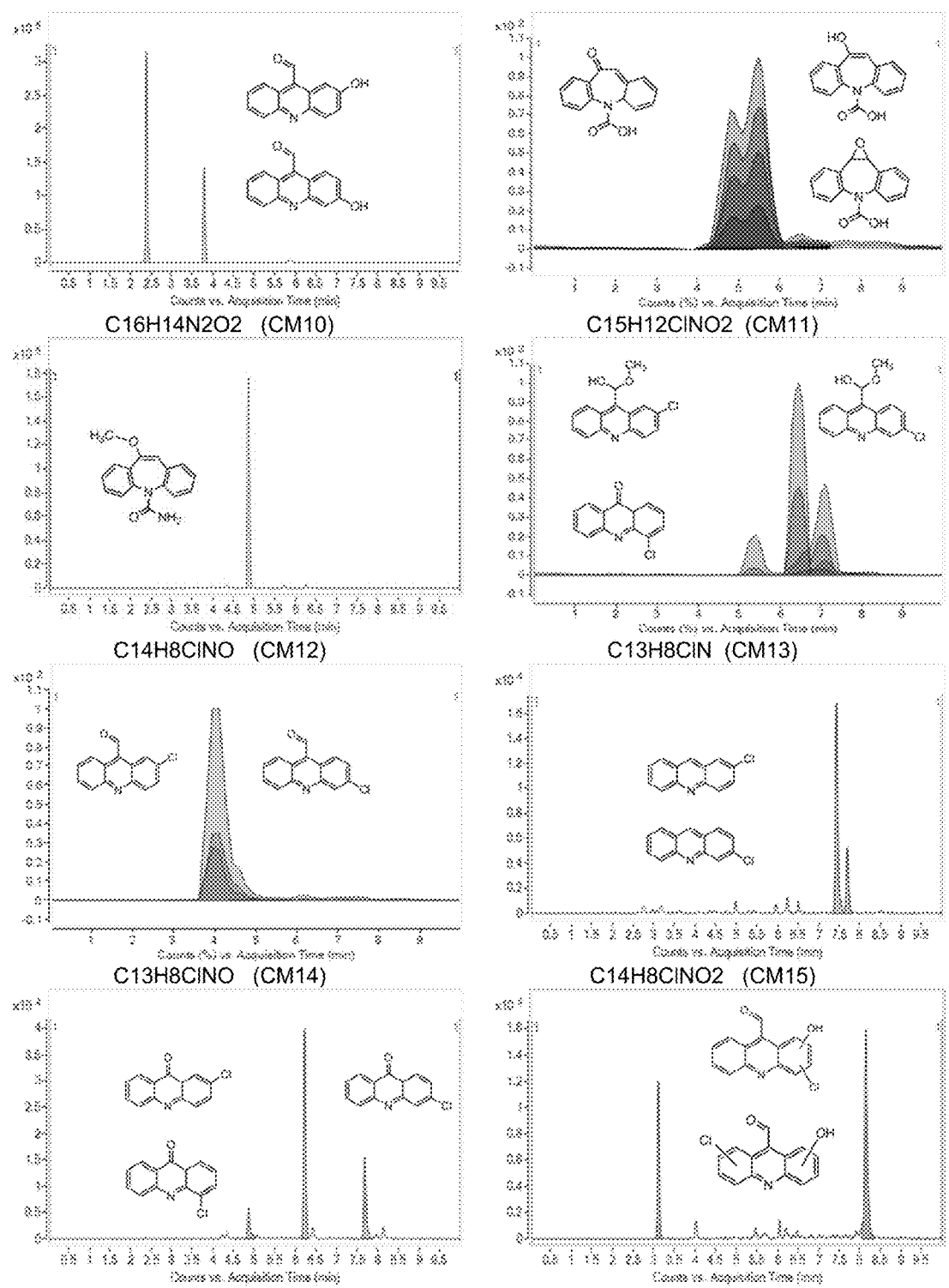
Figure 23:
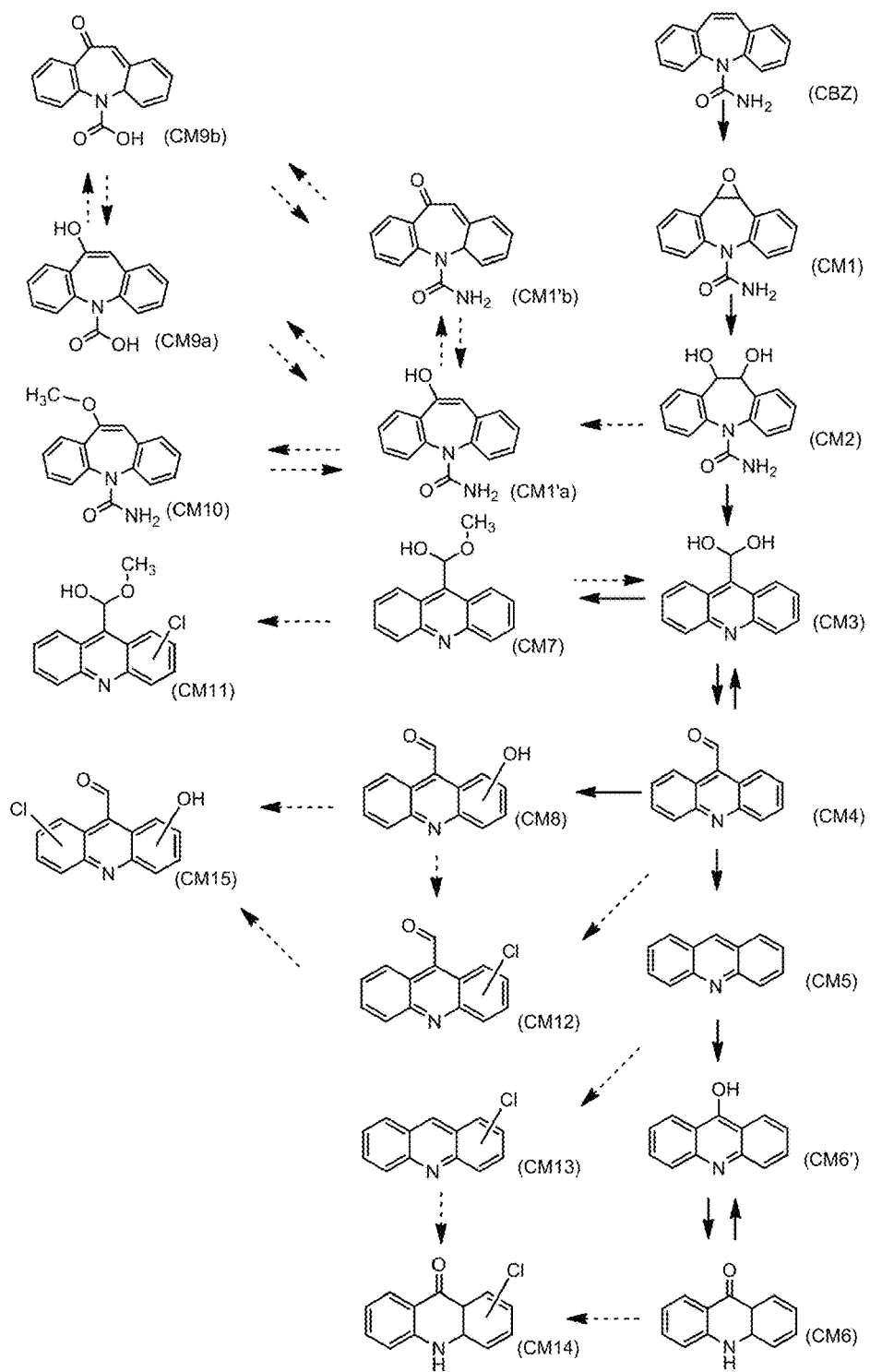
FIG. 23 shows the proposed mechanism of CPO-catalyzed degradation of CBZ.

FIG. 21 shows the chromatograms of CBZ and its metabolites with their proposed structures. In the chromatograms of CM1, CM2, CM9, CM11, CM12, CM13, CM14, and CM15, isomers were identified by their different retention times. CM1, CM9, CM11, and CM12 had problems with signal to noise ratio, which might be due to low concentrations.

FIG. 22 shows the proposed mechanism of CPO-catalyzed metabolism of CBZ.

Discussion

CPO-catalyzed degradation of CBZ was efficient, using nanomolar-level CPO concentrations. CBZ was depleted by 100% using CPO concentration of 2.5 to 14.8 mg/L for 10 min., or ≥96% with 16.5 mg/L for 4 min. The degradation rate and concentrations were conservative: removal ability is mostly likely greater than the parameters of the experiment, as the LC samples were not monitored by shorter time periods.

Compared with some biological treatment in water, such as white rot fungus, the efficiency of degradation was dramatically improved by CPO catalyzation. Strong degradation ability with high concentrations of CBZ using simple conditions (low concentration of catalyst, easy operation, and proper reaction time) show the potential for the composition and method for wastewater treatment.

Example 3—CPO-Catalyzed Degradation of Sulfamethazine

Sulfonamide pharmaceutical substances are widely used in human and veterinary antibacterial treatments. These substances are frequently detected in wastewater and surface water.

Sulfamethazine (SMZ), or sulfadimidine, belongs to a group of heterocyclic sulfonamides. It has been detected in livestock manure and in surface water. Additionally, SMZ-resistant bacteria have been found in water samples, implying that extensive SMZ use has increased the risk of antibacterial resistance and could be detrimental to human health.

To evaluate the CPO—$H_2O_2$—$Cl^-$ system for degradation of antibiotics, the reaction efficiency of CPO in the degradation of SMZ was investigated, and the degradation pathway and structures of metabolites were proposed.

UV-Visible Spectrophotometry

A VARIAN UV-Vis spectrophotometer (Cary 200 Bio) was used to collect the UV spectra of the degradation products. SMZ was dissolved in methanol to make a 3.59 mM stock solution. The drug solution was scanned by dissolving 0.06 mM SMZ in a 100 mM $KH_2PO_4$ buffer with 20 mM KCl at pH 2.75. It was then mixed with 0.06 mM $H_2O_2$. UV spectra were recorded after the addition of 5 nM CPO for 1 min., 2.5 min., and 4 min.

Liquid Chromatography and Mass Spectrometry

To investigate the degradation efficiency, SMZ was dissolved in methanol to make a stock solution (3.59 mM). 62.45 μM (17.38 mg) of SMZ was mixed with 1.3 nM CPO for 30 min. at room temperature. $H_2O_2$ stock solution (41.16 mM) was added to reaction system at 56.5 μL/min. to achieve a final concentration of 314 M $H_2O_2$. The sample was prepared using the same technique described in Example 2. The sample was stored in a freezer at −20° C., or immediately analyzed using a LC-Q-TOF-MS mass spectrometer system.

To detect all metabolites of SMZ, the same experiment above was carried out for 1.5 hours. The filtrate was extracted directly by ethyl acetate, and nitrogen gas purge was used to dry the sample. The dried metabolites were dissolved in 2.0 mL $H_2O$/methanol (95:5 v/v) to produce a concentration of approximately 5 mg/L (ppm). The sample was centrifuged with 1200 g for 10 min. and then 1.5 mL of supernatant were removed by syringe. Filtration was performed using a 0.22 M polyethersulfone syringe filter. The sample was stored in a freezer at −20° C. and analyzed using a LC-Q-TOF-MS system.

To investigate the mechanism of degradation in the CPO—$H_2O_2$—$Cl^-$ system, the sample was prepared with low concentration of $H_2O_2$. 6.86 μM $H_2O_2$ was added directly to Centriprep® centrifugal filter unit (30,000 Dalton cut-off) with 35.90 μM SMZ, catalyzed by 1.3 nM CPO in the 100 mM phosphate buffer with 20 mM KCl, for 1 min., 3 min., and 5 min. Filter units were centrifuged at 3000 g for 1 min. at room temperature, and the filtrate was extracted by ethyl acetate. The organic phase was purged with nitrogen gas to dryness. The dried metabolites were dissolved in $H_2O$/methanol (95:5 v/v) to produce a final concentration of approximately 1 mg/L (ppm), and detected by LC-Q-TOF-MS system immediately. Experiments ran in triplicate.

To investigate brominated products, the reaction was also carried out in a buffer containing KBr instead of KCl, along with 62.45 μM SMZ, 2 mM $H_2O_2$, and catalyzed by 2 nM CPO for 30 min. After the extraction and purge procedure, the final concentration dissolved in the $H_2O$/methanol (95:5 v/v) was ~1 mg/L (ppm).

Instrumentation and chromatographic separation were the same as in Example 1, but without the application of Triple-Quandrupole LC/MS/MS mass spectrometry.

Results

UV-Vis Study of CPO-Catalyzed Degradation of Sulfamethazine

Figure 24:
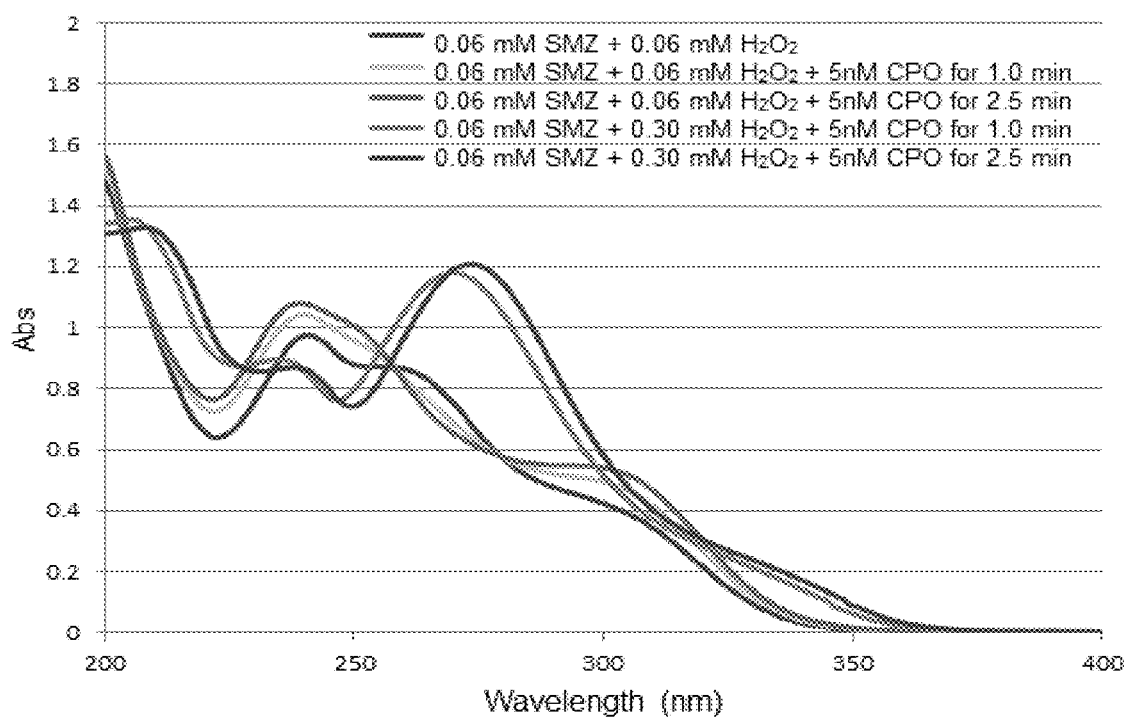
FIG. 24 shows a graph depicting the UV-Vis spectra of CPO-catalyzed degradation of sulfamethazine (SMZ), with its metabolites and $H_2O_2$ at 1 min. and 2.5 min.

The spectra of SMZ showed absorption at 241 nm, 263 nm, and 306 nm. 1 min. after addition of 5 nM CPO, the 241 nm absorption increased, and stopped increasing at 2.5 min., while the 263 nm peak kept decreasing. The wavelength at 306 nm increased from 1 min. to 2.5 min. The UV spectrum at 4 min. was monitored, and was the same as the wavelength at 2.5 min. $H_2O_2$ was added to the mixture solution, to increase the total concentration of $H_2O_2$ to 0.30 mM. After 1 min., the 241 nm peak decreased and a strong absorption was observed at 273 nm (FIG. 24). There was no wavelength that could be used to measure the kinetic parameters of SMZ degradation catalyzed by CPO.

The same reaction was carried out under the same conditions except for the absence of a chlorine ion (KCl) in the phosphate buffer. Without KCl, the absorbance did not change after the addition of CPO. The chlorine ion is imperative in the degradation of SMZ in the CPO—$H_2O_2$—$Cl^-$ system.

CPO—H$_2$O$_2$—Cl$^-$ System

The degradation efficiency of SMZ in CPO—H$_2$O$_2$—Cl$^-$ system was investigated. The sample was analyzed by LC-Q-TOF-MS and SMZ was not observed. Thus, the degradation efficiency of 100% by nanomolar levels of CPO was achieved, suggesting the potential for application of CPO in large-scale wastewater treatment.

LC-Q-TOF-MS

Samples were detected in Agilent Technologies 6530 Accurate-Mass LC-Q-TOF-MS in full scan MS mode, the accurate mass data of the molecular ions were processed through the Agilent MassHunter Qualitative Analysis software. To detect all metabolites, samples were concentrated by five-fold. There were 8 SMZ metabolites (coded SM1 to SM8), confirmed by different retention times and accurate mass-to-charge ratios (m/z). SM9 was detected only in the reaction with limited H$_2$O$_2$ within 5 min. as an intermediate product. FIG. 25 shows the elemental formula, retention time, relative mass difference between the observed mass and the mass of the target compound (in ppm), and the difference between the observed mass and the mass of target compound (in milliDaltons), as collected.

The relative mass differences of the standard drug (SMZ) and metabolites were less than 4.0 ppm. The mass differences of all compounds were less than 1.0 mDa. This method was proved to be efficient for determining the metabolites of SMZ.

Figure 26:
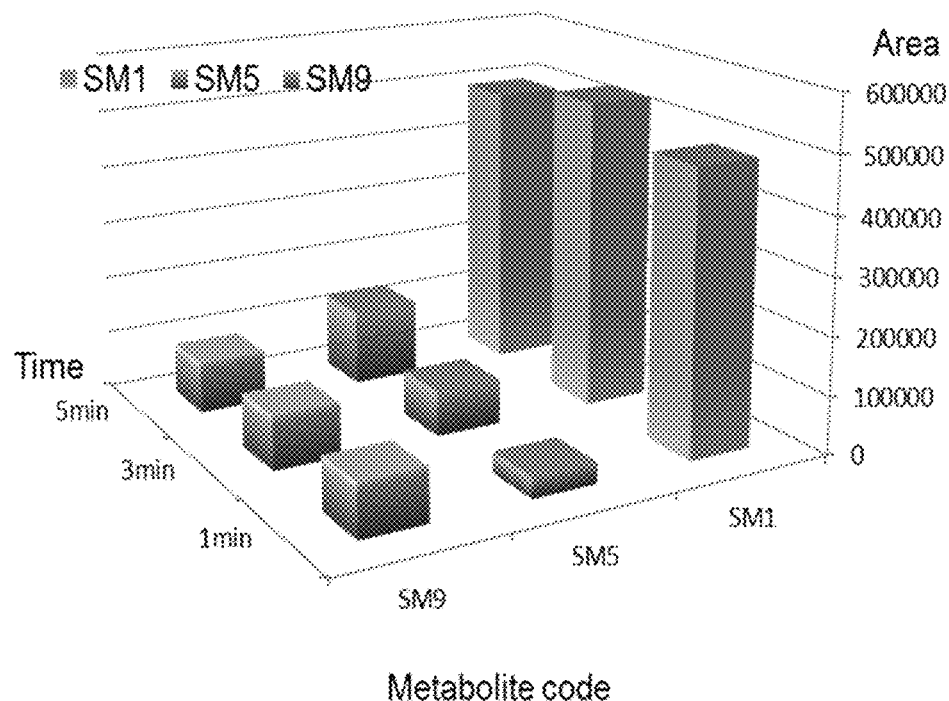
FIG. 26 shows a graphical depiction of the area of SMZ metabolites with limited $H_2O_2$ at 1 min, 3 min, and 5 min detected by Accurate-Mass LC-Q-TOF-MS.

As shown in FIG. 26, to investigate the mechanism of the degradation process, the experiment was carried out for a limited reaction time (1, 3, and 5 minutes) with low concentration of H$_2$O$_2$ (6.86 μM). The ratio of drug concentration to H$_2$O$_2$ concentration was about 5:1.

Figure 27:
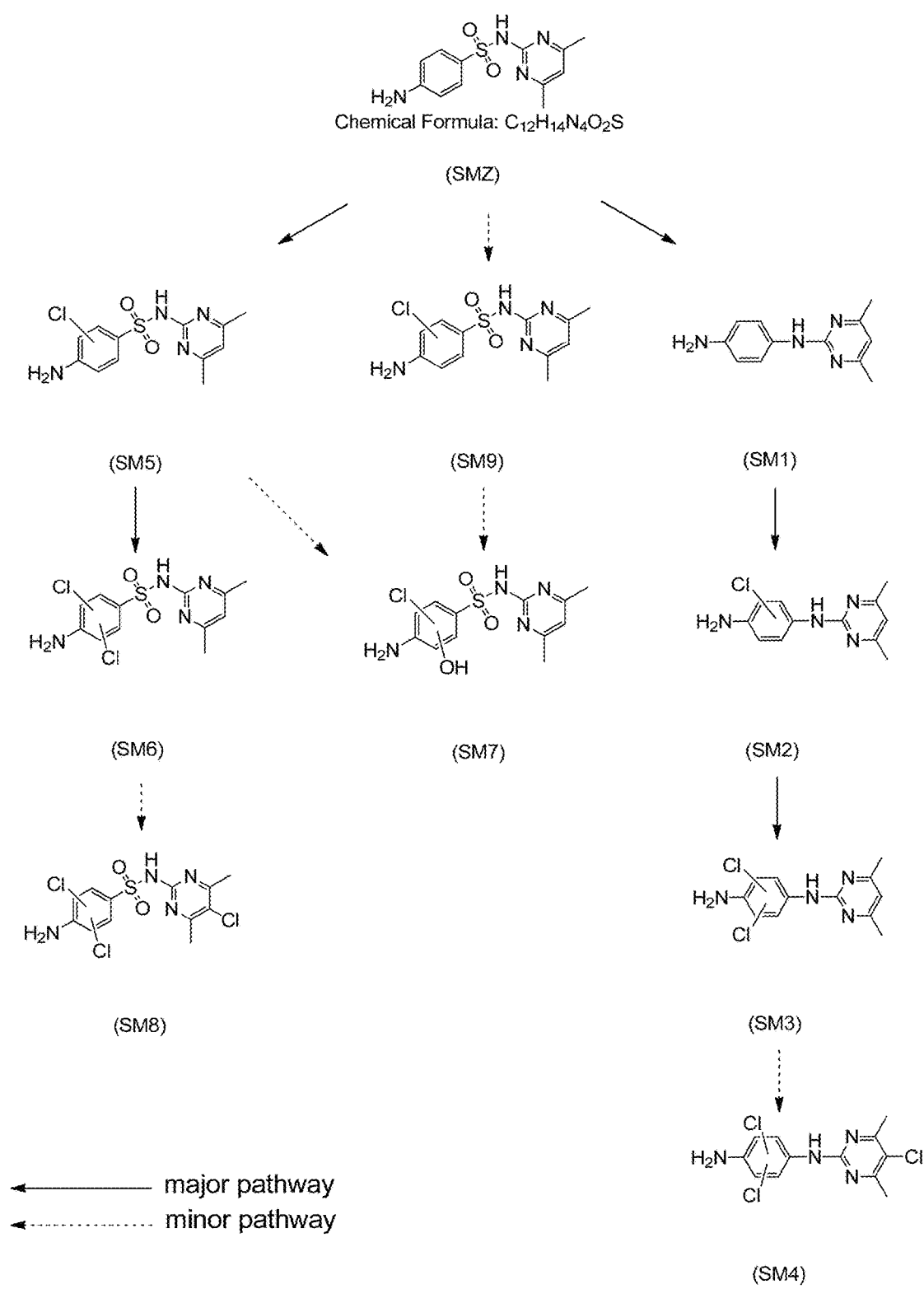
FIG. 27 shows the proposed mechanism of the degradation of SMZ catalyzed by a CPO—$H_2O_2$—$Cl^-$ system, represented by the primary structure of each metabolite.

FIG. 27 shows the proposed pathway for SMZ metabolism catalyzed by CPO, with each metabolite shown by one of its proposed chemical structures. For the CPO—H$_2$O$_2$—Cl$^-$ system, the major pathways were the chlorinated steps with one and two chlorine atom addition and desulfonylation of SMZ. The minor pathway was hydroxylation and chlorination with three chlorine atoms.

CPO—H$_2$O$_2$—Br$^-$ System

Figure 29:
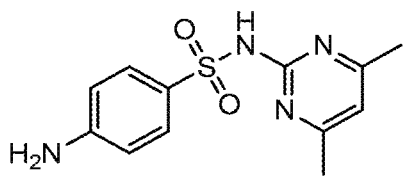
FIG. 29 shows the mechanism of CPO-catalyzed bromination of SMZ.
Figure 29:
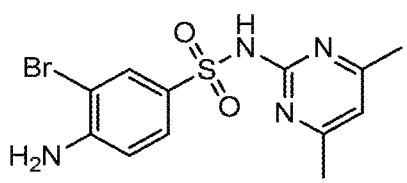
Figure 29:
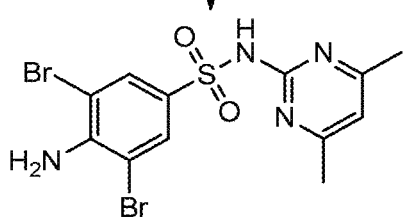
Figure 29:
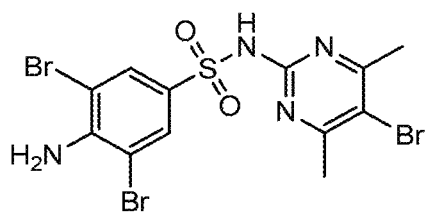

To investigate the halogenation of SMZ catalyzed by CPO, 20 mM KBr was applied in the buffer instead of KCl. The CPO—H$_2$O$_2$—Br$^-$ system reaction was carried out at room temperature, and the product spectrum was obtained. As shown in FIG. 28, there were only 3 metabolites detected, all of which were brominated products. The ratios of the molecules containing three bromine atoms were 1:3:3:1. As shown in FIG. 29, which depicts the mechanism of SMZ bromination catalyzed by CPO, there was only one pathway to elucidate the mechanism of SMZ halogenation.

Discussion

The process of CPO-catalyzed SMZ degradation was efficient. 100% depletion of SMZ was achieved by a nanomolar level of CPO. The degradation rate and substrate concentrations were conservative: removal capability was mostly likely greater than the parameters used in the experiment because LC samples were not monitored by a shorter time period.

Compared with some biodegradation treatment in water, such as white rot fungus, the efficiency of CPO-catalyzed reaction was dramatically improved. Given the nanomolar amount of enzyme required and the rapid sample preparation, CPO-catalyzed degradation can be used in large-scale wastewater treatment.

Figure 30A:
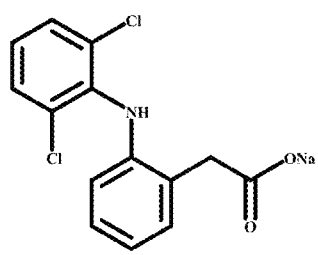
FIG. 30A shows the chemical structure of diclofenac.
Figure 30B:
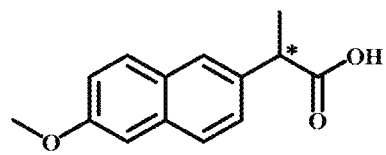
FIG. 30B shows the chemical structure of naproxen.

Example 4—Degradation of Non-Steroidal Anti-Inflammatory Drugs Diclofenac and Naproxen by CPO FIG. 30A shows the chemical structure of diclofenac, and FIG. 30B shows the chemical structure of naproxen. Diclofenac (2-[(2,6-dichlorophenyl)amino]benzeneacetic acid; sodium salt) and naproxen (2-(6-methoxynaphthalen-2-yl)propionic acid) are non-steroidal anti-inflammatory drugs (NSAIDs), widely used for the treatment of arthritis, ankylosing spondylitis, and acute muscle pain. However, most NSAIDs are usually not completely metabolized by the human body, and simply pass through. Furthermore, these compounds are difficult to break down using general waste treatment strategies.

The following is a study of the degradation of diclofenac and naproxen by CPO. The major degradation products were identified and reaction pathways were postulated. Results demonstrated that CPO can effectively convert both diclofenac and naproxen into compounds that are significantly less toxic based on their inhibitory effects and EC50 value on the growth of a freshwater green alga, *Chlorella pyrenoidos*.

Experimental Materials and Methods

CPO was isolated from the growth medium of *C. fumago* according to the method of Morris and Hager (1966) with minor modifications, using acetone rather than ethanol in the solvent fractionation step. CPO with Rz=1.03 (A398/A280, 1.44 for pure enzyme) was prepared and stored in 100 mM phosphate buffer (pH 5.0) at 4° C.

The halogenation activity of CPO used in this study was 4232 U·mL$^{-1}$ based on the standard MCD assay (Hager et al., 1966). The aromatic hydroxylation activity (3563 U·mL-1) of the enzyme was determined by monitoring the hydroxylation of naphthalene into I-naphthol (Kluge et al., 2007). The classic peroxidase activity of the enzyme determined using ABTS as the substrate was 3071 U·mL$^{-1}$ (Manoj et al., 2008).

All reagents used in this study, including diclofenac, naproxen, dipotassium hydrogen phosphate, potassium dihydrogen phosphate, hydrogen peroxide (30% in aqueous solution), ethyl acetate, and inorganic reagents for cultivating the green alga were obtained from Xi'an Chemical Co. Ltd (Xi'an, China) with highest purity (≥98%). Other chemicals, such as methanol and acetonitrile (chromatography grade), as well as standard degradation products of the two drugs, o-desmethylnaproxen and 4'-hydroxydiclofenac (chromatography grade), were purchased from Sigma Aldrich (St. Louis, Mo. USA).

Phosphate buffer (0.1 mol·L$^{-1}$) was prepared by mixing appropriate volumes of 1 mol·L$^{-1}$ KH$_2$PO$_4$ and K$_2$HPO$_4$ stock solutions and diluting the combined solutions to 1 L. The solution was adjusted to various pH with 1 mol·L$^{-1}$ H$_3$PO$_4$. All solutions were prepared using deionized water with a conductivity of 5.6×10-8 s·cm-1.

Degradation of Diclofenac and Naproxen

Enzymatic degradation of both drugs was carried out in 0.1 mol·L-1 phosphate buffer in a centrifugal tube with a total volume of 3.0 mL containing CPO (0.25-0.23 nmol·L-1), 20 mmol·L-1 KCl, and drugs (15 μmol·L$^{-1}$) at pH 2~6 at 298K. The reaction was started by adding H$_2$O$_2$ (0.015-0.3 mmol·L$^{-1}$) in the absence of light under magnetic stirring and was continued for 20 min. The supernatant of the reaction mixture was extracted 3 times using ethyl acetate. The combined organic extract was concentrated by rotary evaporation (0.09 MPa, 308K) to remove the solvent. The extracts were then dissolved in acetonitrile and methanol, respectively, for HPLC (LC-20AT, Shimadzu) analysis. The mobile phase consisted of 80:20 (v/v) acetonitrile and water for diclofenac and 90:10 (v/v) methanol and water for naproxen, and the flow rate was 0.5 ml·min$^{-1}$. The detector was set at 274 nm and 235 nm for diclofenac and naproxen, respectively. The quantitative analysis of the target compounds was based on the standard curve (correlation coefficients were >0.999). The effect of reaction parameters (pH, concentration of enzyme/$H_2O_2$, and reaction time) on degradation efficiency was investigated and optimized.

All experiments were triplicated and data reported were mean values of three independent measurements.

Determination of Products

Samples were treated as above for HPLC-MS analysis. An Esquire LC-ion trap mass spectrometer (Bruker Daltonics, Germany) equipped with an orthogonal geometry Electrospray Ionization (ESI) source was employed to determine the formulae of the products. Nitrogen was used as the drying (8 L·min$^{-1}$) and nebulizing (0.8 bar) gas at 180° C. Scanning was performed from m/z 100 to 1000 in the standard resolution mode.

To establish the structure of the degradation products, the reaction was carried out using the same condition as stated above except a larger volume (300 mL) was used. Upon completion of the reaction, the reaction mixture was extracted with either ethyl acetate or chloroform. After removal of the solvent by rotary evaporation (0.09 MPa, 308K), the extracts were dissolved in either deuterated chloroform or methanol and transferred to 5 mm NMR tubes. NMR experiments were carried out on a Bruker 600 MHz NMR spectrometer operating at a proton frequency of 599.73 MHz. All spectra were recorded at 298 K using standard pulse programs from the manufacturer.

Elimination of COD and TOC

Total organic carbon (TOC) measurement was conducted on a TOC-VCPA analyzer (Shimadzu Corp.). The feed speed was 150 ml·min$^{-1}$. Chemical oxygen demand (COD) was measured by a quick method on a Rapid Autoanalyzer (5B-1(F), Lian-hua Tech. Co., Ltd). A solution containing 2.5 ml sample, 0.7 ml reagent D (potassium dichromate) and 4.8 ml reagent E (catalysts) in a 20.0 ml glass tube was heated to 438K and kept for 10 min. together with a blank sample and a standard sample. After 2 min. of air cooling, the heated solution was cooled by water for another 2 min. Then the absorbency of the samples was measured at 610 nm.

Treatment of Drug Effluent by Activated Sludge

A mixed population of activated sludge microorganisms was collected from Xi'an second sewage treatment plant (Xi'an, China). The sample of activated sludge was filtered on a Spectra Mesh polypropylene 149-μm filter (Spectrum Laboratories Inc., Rancho Dominguez, Calif., USA) to remove aggregates. The sample was then washed three times by centrifugation and suspended in the same volume of culture medium. To remove any excessive amounts of dissolved organic carbon, the suspension was stirred and maintained under oxygen at 298K for at least 24 h without exposure to the test materials. The volatile ratio f of activated sludge was 0.74.

90 mL of 15 μmol·L$^{-1}$ drug effluent was put into the activated sludge suspension before/after enzymatic treatment (to ensure a final drug concentration of 7.5 μmol·L$^{-1}$). The samples were stirred for the duration of the study with a magnetically coupled stirrer when air was used as the aerated gas. The sample was then left to stand for 1-2 h. The supernatant was taken for determination of COD.

Toxicity Tests

Freshwater unicellular green alga, *C. pyrenoidosa* (provided by the Institute of Wuhan Hydrobiology, Chinese Academic of Science), was cultivated in nutrient media of blue green medium (BG11) at 298K and illuminated with cool-white fluorescent lights at a continuous light intensity of 2000 Lx. For cell experiments, *C. pyrenoidosa* was exposed, during its log growth phase, to the toxicant at five different concentrations (maintain final concentration ranging from 0.01 to 0.36 mg/L) for 3-4 days at 298K. The concentration of the alga was determined by monitoring the change of absorption at 680 nm (Ma et al., 2006). The toxicity tests for each drug concentration were conducted in triplicate.

The growth inhibition rate for each sample was calculated. EC50 (drug concentration required to cause 50% reduction in growth) values were calculated using linear regression analysis of drug concentration as natural logarithm versus percentage inhibition. All correlation coefficients were >0.99.

Results

Effect of Reaction Parameters on Drug Degradation

Since various physicochemical parameters influence the degradation efficiency, it is essential to optimize these factors in order to make the process more efficient and practically applicable.

FIGS. 31A-31D generally show the relationship between degradation efficiency and reaction condition of CPO-catalyzed degradation of diclofenac (left) and naproxen (right).

Figure 31A:
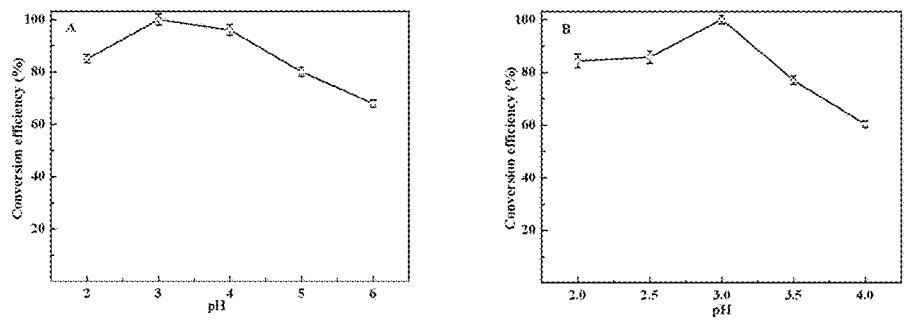
FIGS. 31A-31D generally show the relationship between degradation efficiency and reaction condition of CPO-catalyzed degradation of diclofenac (left) and naproxen (right).

The pH range investigated was 2-6 due to poor stability and activity of CPO at higher pH. FIG. 31A shows that the degradation efficiency of naproxen and diclofenac increased rapidly with increasing pH, and reached maximum around pH 3.2. The degradation efficiency decreased sharply when pH was increased above 3.2.

Figure 31B:
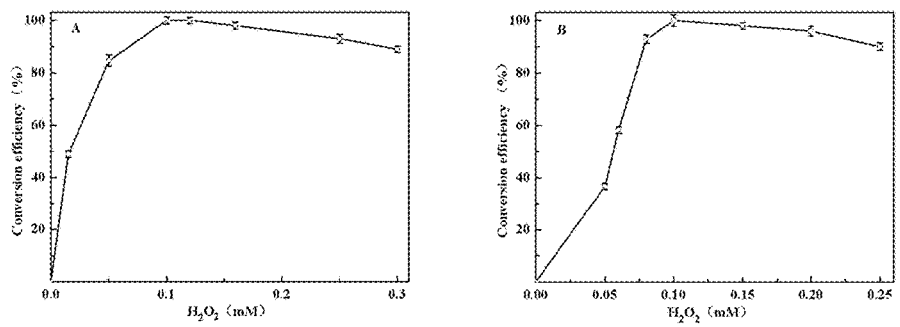

The effect of $H_2O_2$ concentration on CPO-catalyzed degradation of diclofenac and naproxen is shown in FIG. 31B. As expected for all peroxidases, no degradation of either drug was observed before the addition of $H_2O_2$. The degradation efficiency of both drugs increased as $H_2O_2$ concentration is increased. Maximum rate is achieved when total $H_2O_2$ concentration reached 0.1 mmol·L$^{-1}$. Further addition of $H_2O_2$, however, repressed the degradation of both drugs possibly due to formation of Compound III caused by high concentrations of $H_2O_2$ (Ayala et al., 2011). Therefore, 0.1 mmol·L$^{-1}$ of $H_2O_2$ was chosen in the degradation of both diclofenac and naproxen in all subsequent experiments.

Figure 31C:
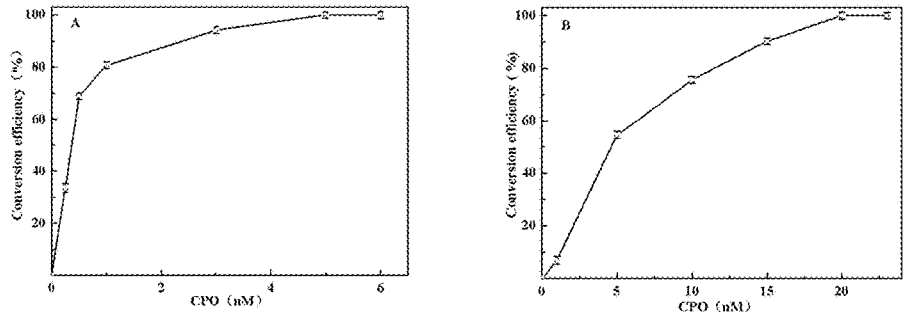
Figure 31D:
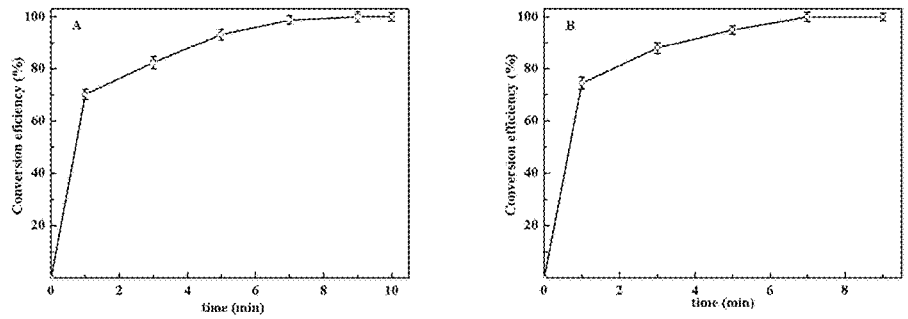

Optimizing CPO concentration not only improves degradation efficiency but also saves cost of operation. The range of CPO concentration tested was 0.25-6.0 nmol·L$^{-1}$ for diclofenac and 1.0-23.0 nmol·L$^{-1}$ for naproxen. FIG. 31C shows that degradation efficiency of both drugs increased rapidly as CPO concentration was increased. Complete degradation of the drugs was achieved when CPO concentration was above 5.0 nmol·L$^{-1}$ for diclofenac, and 20.0 nmol·L$^{-1}$ for naproxen, indicating that CPO is extremely efficient in the degradation of the subject drugs. CPO degrades both diclofenac and naproxen with a remarkable rate. As shown in FIG. 31D, about 70% of diclofenac and 75% of naproxen is degraded within 1 min. The complete degradation was achieved in only 9 and 7 min. for diclofenac and naproxen, respectively, at optimum reaction condition.

Determination of Products by HPLC-MS and NMR

HPLC-MS and NMR analyses were employed to establish the structures of the putative products from the two drugs. CPO-catalyzed hydroxylation of diclofenac and O-demethylation of naproxen were observed.

Figure 32:
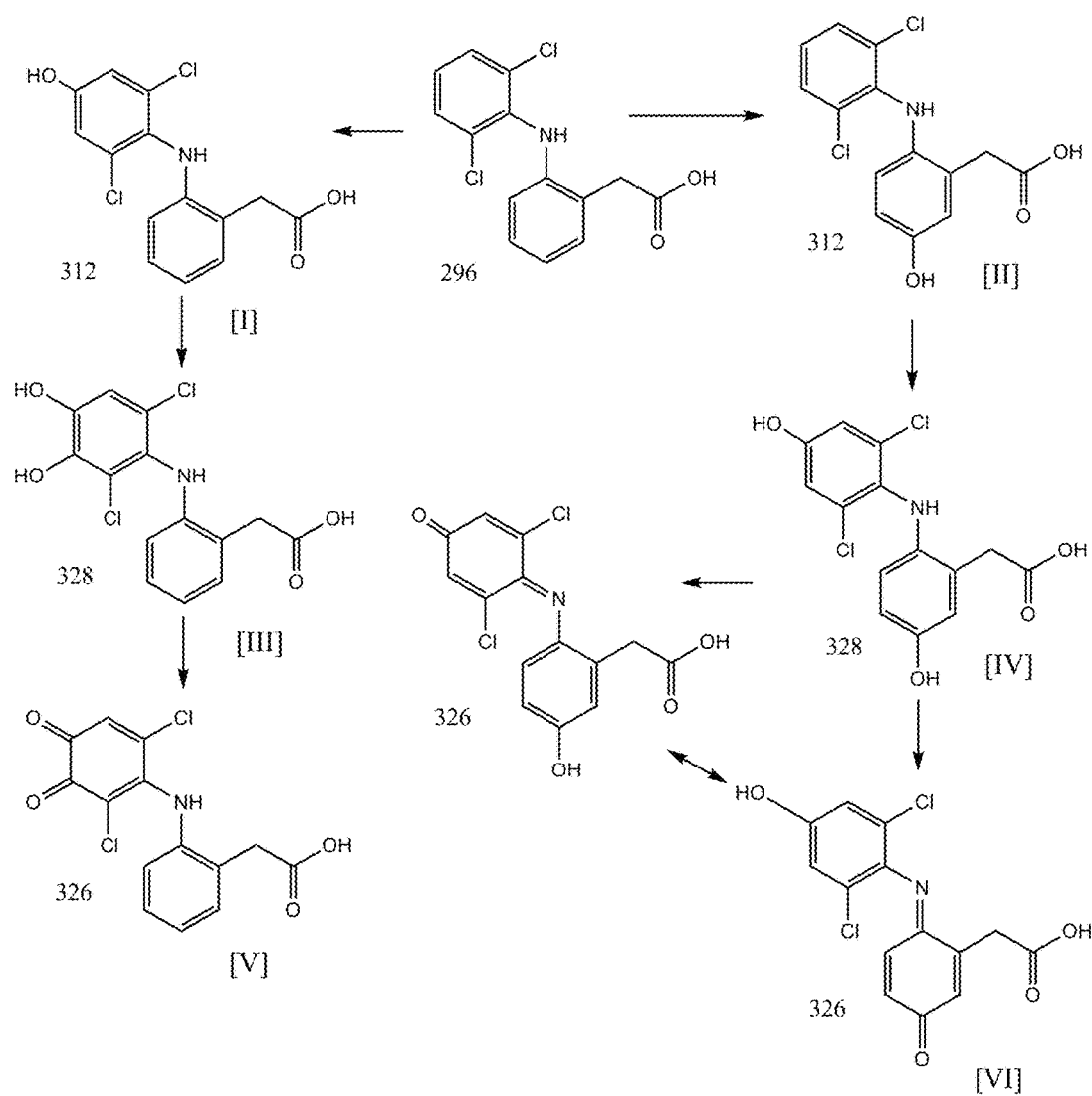
FIG. 32 shows the proposed degradation pathway of diclofenac during CPO-catalytic oxidative process.

FIG. 32 shows the sequence of diclofenac degradation catalyzed by CPO based on the products identified from HPLC-MS and NMR analysis. The diverse catalytic activity of CPO makes it possible to produce a broad array of products from diclofenac degradation, however, under the conditions employed in this study, only hydroxylation activity was observed. This can be appreciated by the similarity between CPO and cytochrome P450 that metabolizes most xenobiotics via hydroxylation. Thus CPO converts diclofenac to either monohydroxylated or dihydroxylated products, the same as the major products observed in the metabolism of diclofenac (Blum et al., 1996; Osorio et al., 2014).

Figure 33A:
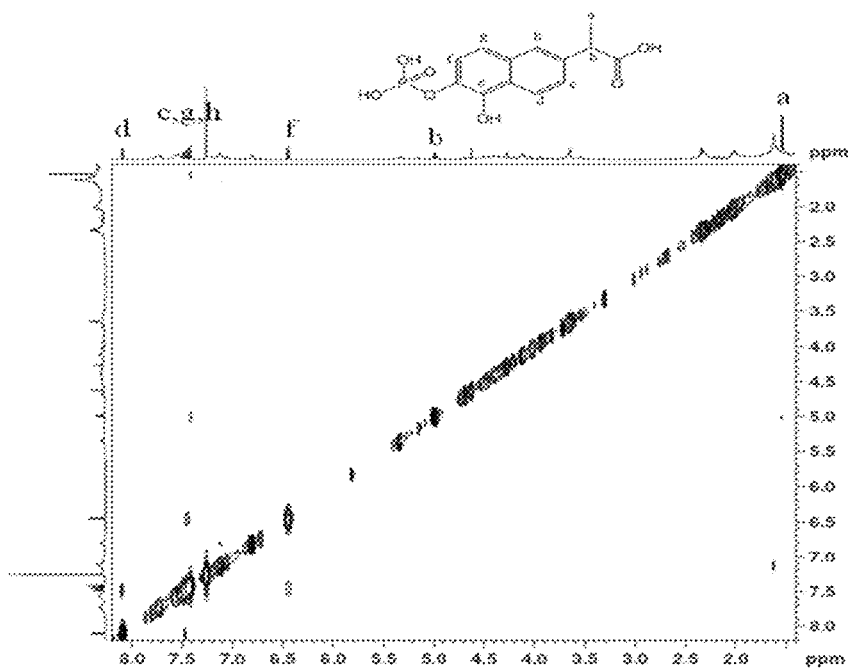
FIG. 33A shows proton nuclear magnetic resonance (NMR) nuclear overhauser enhancement spectroscopy (NOESY) of naproxen product [I]. The weak nuclear overhauser effects (NOEs) between peaks a and c and between peaks b and c can only be observed at lower contour levels. The NOE coupling patterns unequivocally define the structure of this degradation product.
Figure 33B:
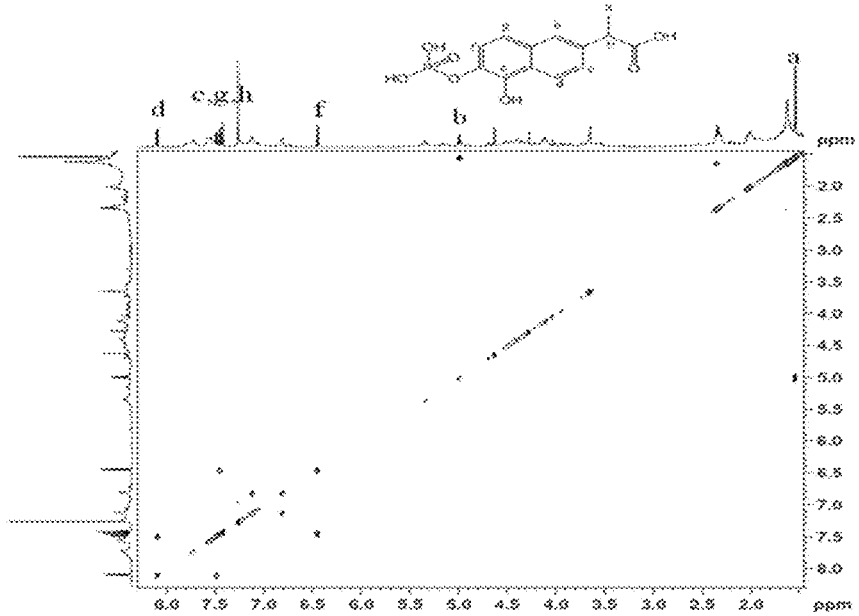
FIG. 33B shows proton NMR correlation spectroscopy (COSY) of naproxen product [I].
Figure 34:
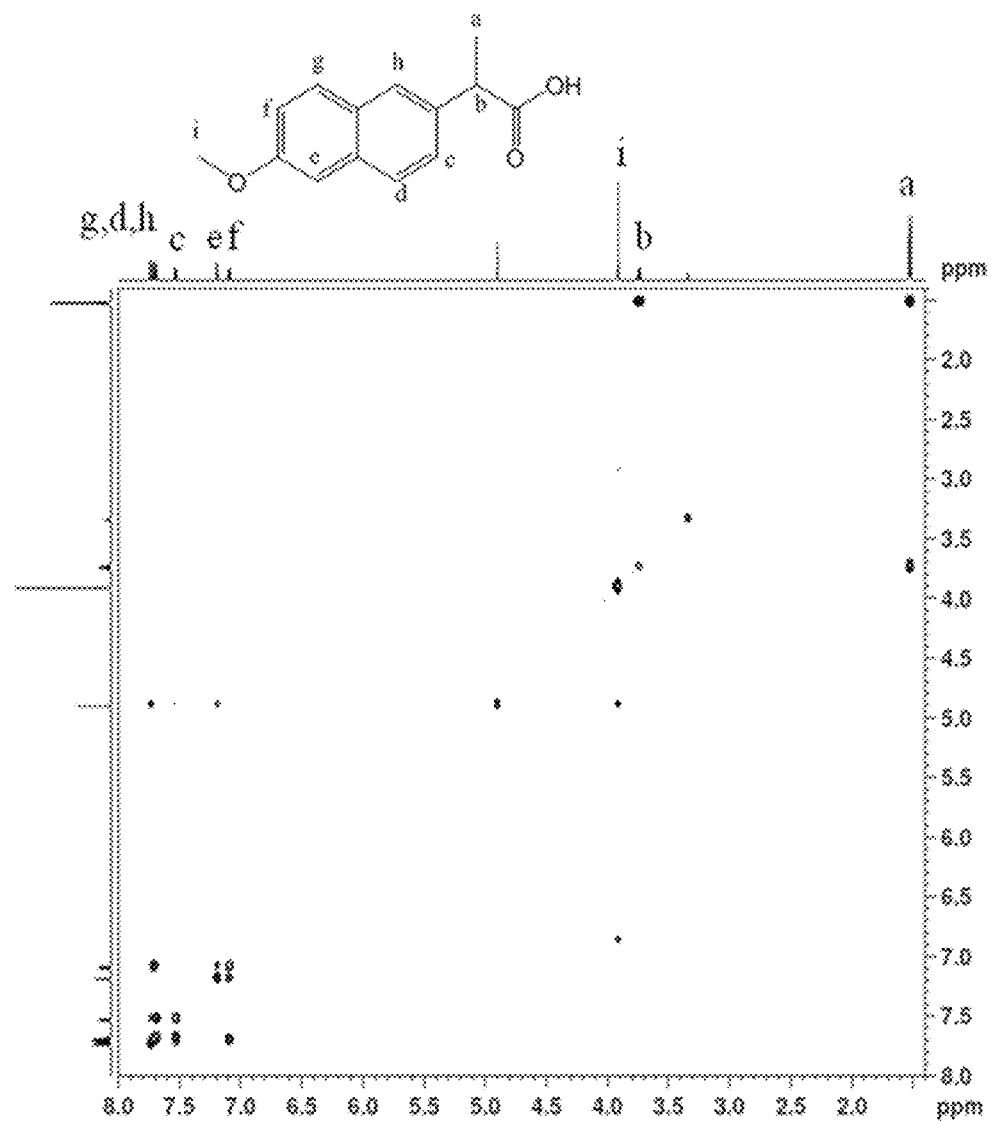
FIG. 34 shows COSY of naproxen.
Figure 35:
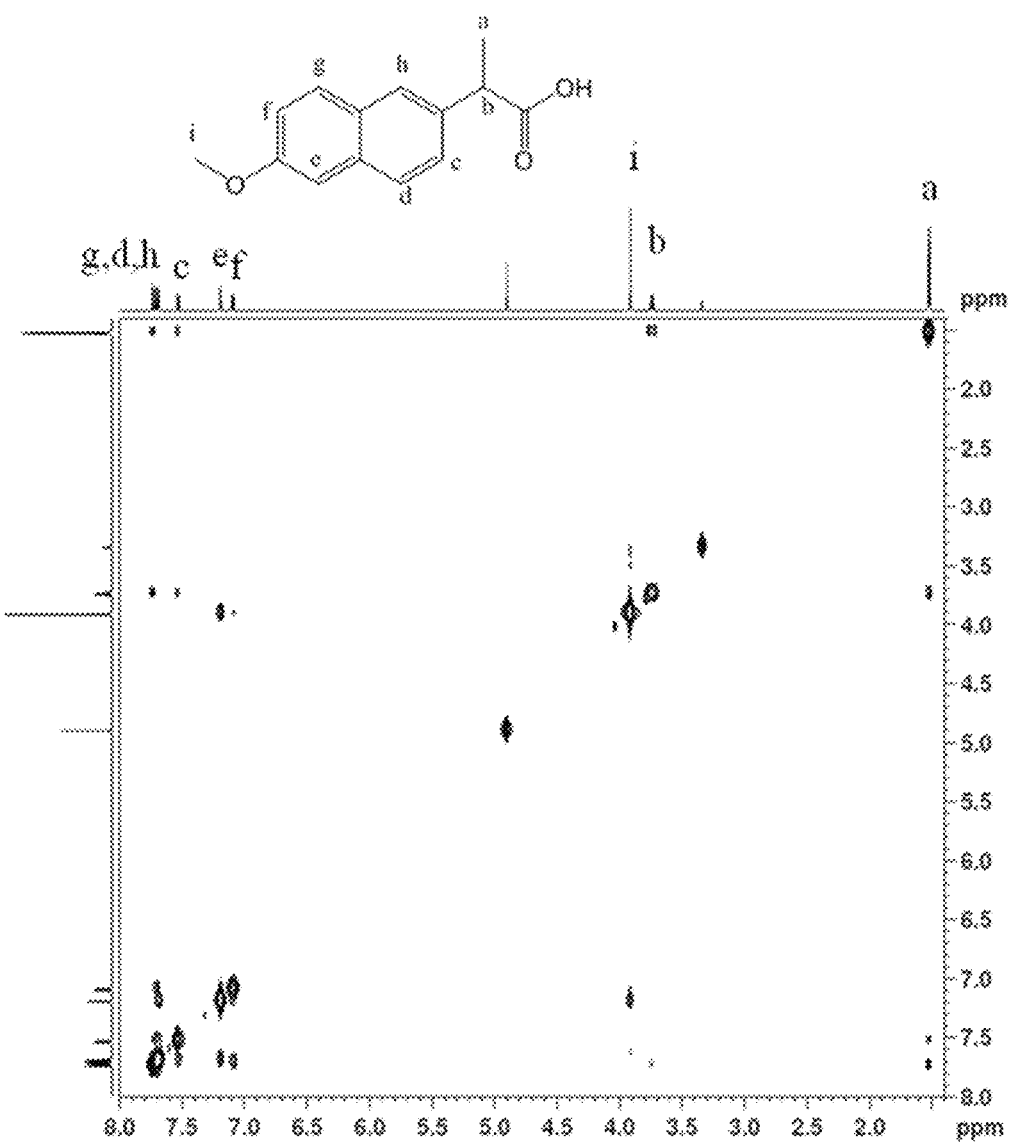
FIG. 35 shows NOESY of naproxen.

The identification of products from CPO-catalyzed degradation of naproxen was achieved by detailed NMR analysis of the products with the aid of MS. FIGS. 33A and 33B show proton NMR NOESY spectra and COSY spectra of naproxen product [I], respectively. The most noticeable difference between proton NMR spectra of the products and the parent drug, naproxen, is the absence of the methoxy signal (peak "i" around 3.9 ppm, as shown in FIGS. 34 and 35) in the products. This suggests the demethylation of naproxen.

Although CPO catalyzed N-demethylation has been reported (Kedderis et al., 1980), the observed O-demethylation represents novel CPO activity. This is reminiscent of the activity displayed by P450 (Meunier et al., 2004) and UPOs (Hofrichter et al., 2014; Kinne et al., 2009) that are structurally related to CPO.

Figure 36:
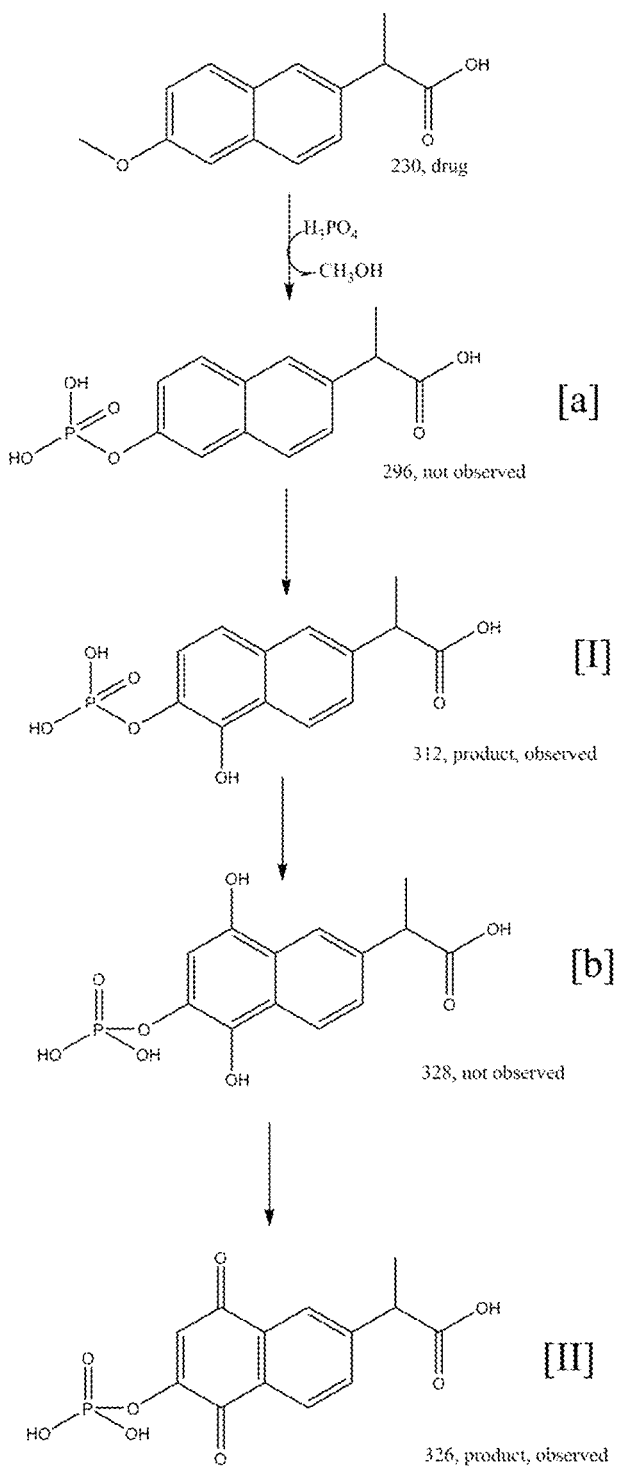
FIG. 36 shows the proposed degradation pathway of naproxen during the CPO-catalytic oxidative process.

Based on the major products identified from that study, the reaction sequence of naproxen degradation catalyzed by CPO was proposed, as shown in FIG. 36. Similar to the degradation of diclofenac, CPO catalyzed degradation of naproxen is achieved primarily via CPO's monooxygenase activity. Thus, CPO degrades naproxen to either monohydroxylated or dihydroxylated products, similar to the major products observed in bacterial degradation of naproxen (Wojcieszyńiska et al., 2014). Initially, naproxen was degraded to desmethylnaproxen (Aresta et al., 2006; Urrea et al., 2010).

The products identified in the above NMR and MS analysis are subjected to further oxidative transformation as supported by the results from activated sludge experiment as well as eco-toxicity test.

Reduction in Chemical Oxygen Demand (COD) and Total Organic Carbon (TOC)

FIG. 37 showed that only 4.9%, 9.1% of COD and 25%, 7.6% of TOC removal was achieved for diclofenac and naproxen, respectively. It is therefore proposed that CPO catalyzed degradation can serve as an efficient pre-treatment step in waste water treatment. This can be combined with subsequent bioremediation technologies (activated sludge) for complete decontamination of the two drugs in waste water.

Combined Treatment of Drug Effluent by Enzymatic Oxidation and Activated Sludge

As indicated in FIG. 37, the COD value of drug effluent did not decrease noticeably after CPO-treatment. However, compared with the parent drugs, the products from CPO catalyzed degradation have improved solubility in aqueous media and are more vulnerable to further biodegradation. This conclusion was confirmed by the observation that treatment of CPO-catalyzed reaction mixture with activated sludge increased COD removal from 4.9% and 9.1% to 85% and 86% for diclofenac and naproxen, respectively. On the other hand, treatment by activated sludge alone only removes 49% and 54%, of the COD for diclofenac and naproxen, respectively, suggesting that more effective decontamination of the two drugs can be achieved through CPO pre-treatment followed by existing bioremediation technologies (activated sludge).

Evaluation of the Eco-Toxicity of the Products

In some cases simple destruction of a drug is inadequate, since the resulting products may also be highly toxic, and special attention must therefore be paid to toxicity assessment of products to ensure that the agent has been effectively detoxified. However, toxicity evaluation about the products from diclofenac and naproxen are not readily available. Biological assays offer a direct measure to evaluate the magnitude of the potential health risk of chemicals. Therefore, a growth-inhibitory test was carried out using *C. Pyrenoidosa*.

Figure 38:
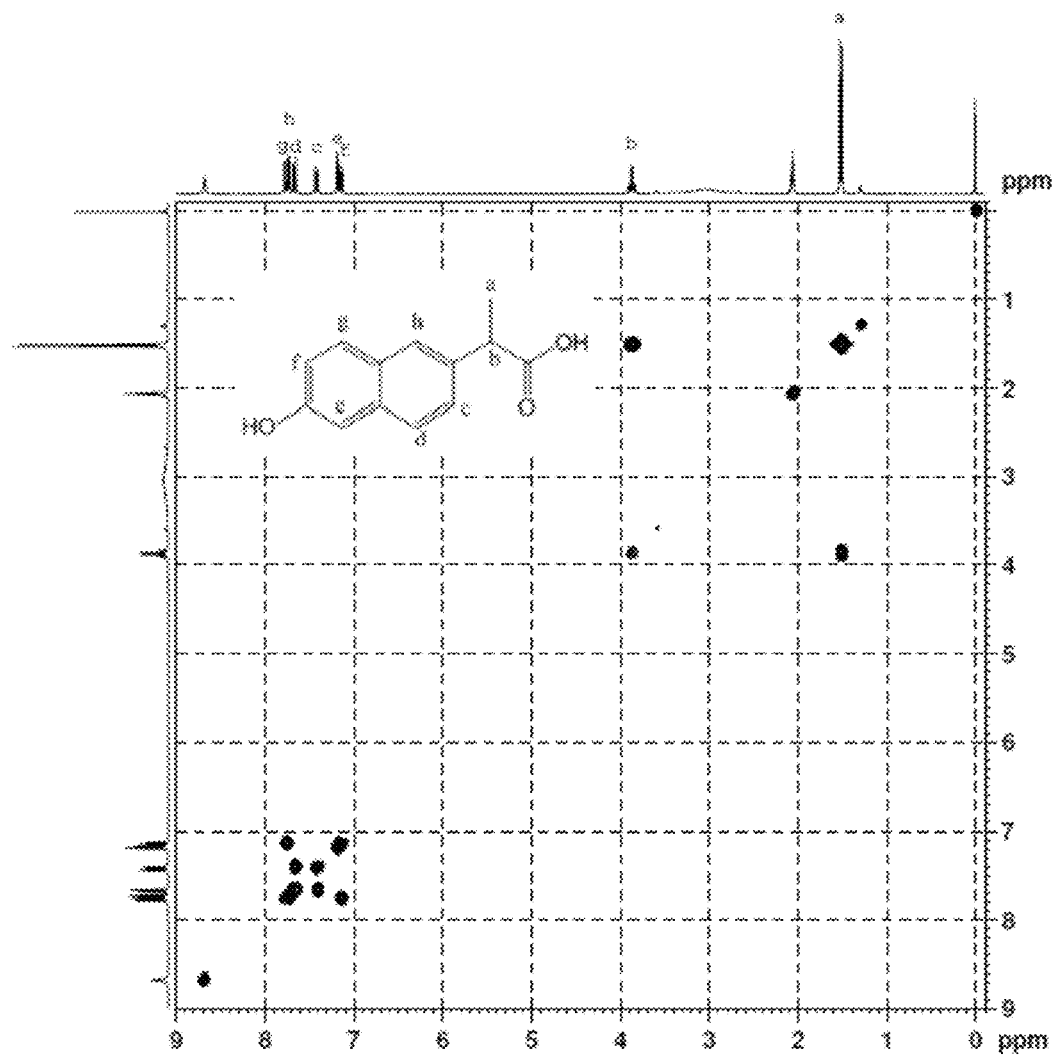
FIG. 38 shows COSY of authentic desmethylnaproxen purchased from Sigma Aldrich.

FIG. 38 shows COSY of authentic desmethylnaproxen purchased from Sigma Aldrich. This showed that the 72-h $EC_{50}$ increased with the increase in degradation efficiency. The value was 0.25 mg·L$^{-1}$ for diclofenac and 0.33 mg·L$^{-1}$ for naproxen at the end of degradation. These results demonstrated that the products had lower toxicity compared with the parent drugs, suggesting the great potential of using CPO as an efficient catalyst in the safe removal of these drugs from environmental.

Discussion

This study demonstrated that CPO catalyzed oxidative degradation is a promising alternative for treatment of waste water containing non-steroidal anti-inflammatory drugs. Complete degradation of diclofenac and naproxen is reached in only 9 and 7 min, respectively, under mild conditions.

The products identified by HPLC-MS suggested the initial hydroxylation of the drug molecules followed by further oxidative transformation. The biodegradability of the decomposition products was significantly increased as confirmed by COD measurement after combining the enzymatic oxidation with activated sludge treatment. Most significantly, the products of both diclofenac and naproxen had dramatically lower toxicity than the original drugs as judged by the 72-h $EC_{50}$ value of *C. Pyrenoidos*. Our results demonstrate that CPO can serve as an efficient, cost-effective, and environmentally friendly catalyst for large-scale treatment of waste water contaminated with the two drugs studied.

Example 5—MTT Assays of Acetaminophen, Carbamazepine, and Sulfamethazine

Experimental Materials and Methods

Cells (MDA-MB-231 Breast Cancer Cells; 2×105) were plated in 6-well plates in DMEM containing 10% FBS. Cells were incubated in the absence or in the presence of different amounts (0 to 2 μg/ml) of different compounds as showed in the figure for 24 h.

Cells were exposed to 10 mg/ml MTT [3-(4,5-dimethylthiazol-2-yl)-2,5-diphenyl tetrazolium bromide] for the last 4 h. After incubation, the medium was removed and formazan crystals were dissolved in detergent reagent following the manufacturer's instructions (ATCC). Optical density for each condition was determined at 570 nm.

Figure 39A:
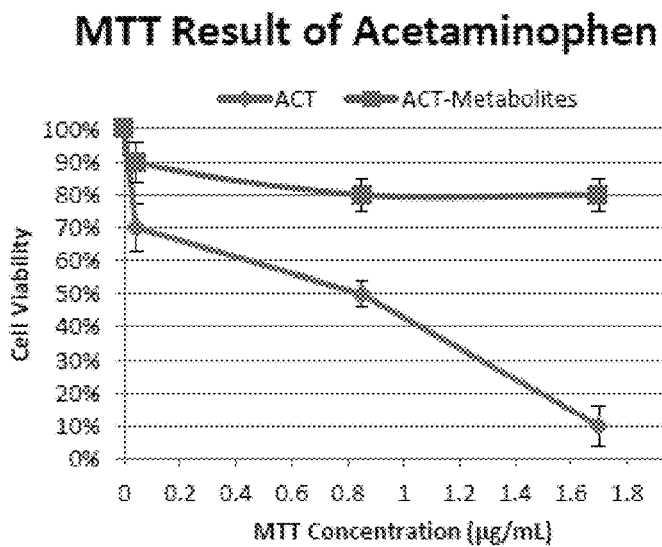
FIGS. 39A, 39B, and 39C show levels of cell viability with regard to increasing MTT (3-(4,5-dimethylthiazol-2-yl)-2,5-diphenyltetrazolium bromide) concentration for APAP, CMZ, and SMZ, respectively, compared with their metabolites.
Figure 39B:
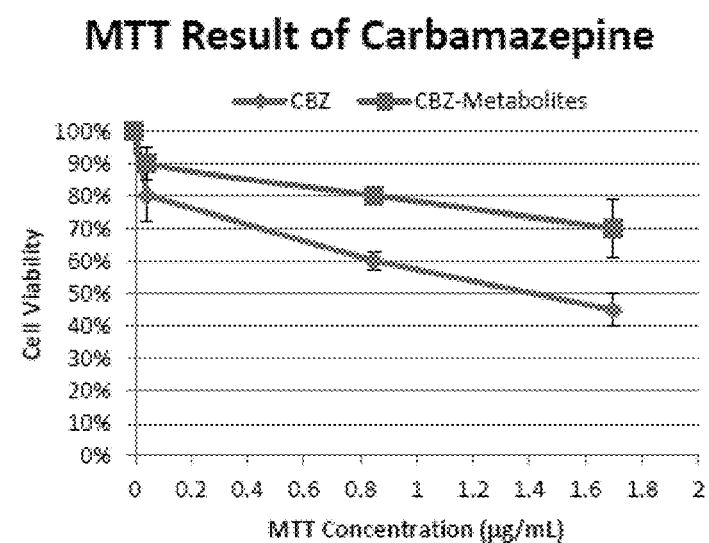
Figure 39C:
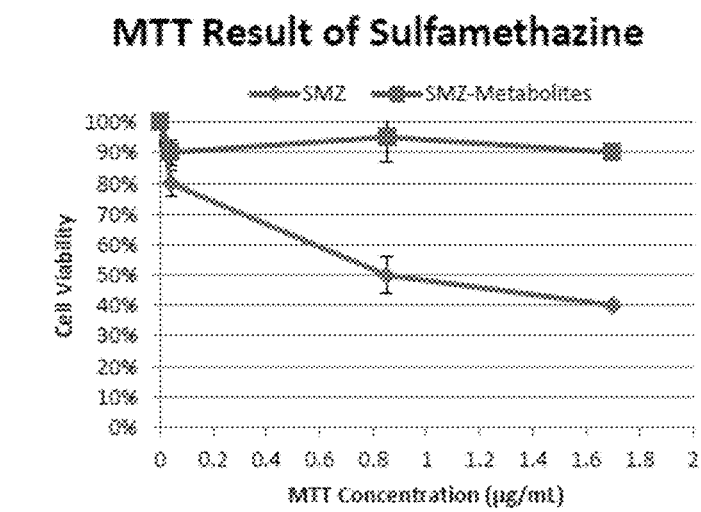

MTT incorporation was expressed as percentage of the control in the absence of compounds. DMSO (0.04%) and methanol (0.001%) were used as control since these compounds were dissolved on them at 10 mg/mL. The concentration is expressed in μg/ml as percentage of control (100% methanol was added at 0.001%). FIGS. 39A, 39B, and 39C show levels of cell viability for each drug with respect to increasing MTT concentration for ACT and ACT metabolites.

Results

| Acetaminophen (ACT) | | | | |
|---|---|---|---|---|
| MTT (µg/ml) | ACT | ACT-Metabolites | ACT-SD | ACT_met-SD |
| 0 | 100% | 100% | 4.00% | 8% |
| 0.0425 | 70% | 90% | 6.00% | 7% |
| 0.85 | 50% | 80% | 5.00% | 4% |
| 1.7 | 10% | 80% | 5.00% | 6% |

| Carbamazepine (CBZ) | | | | |
|---|---|---|---|---|
| MTT (µg/ml) | CBZ | CBZ-Metabolites | CBZ-SD | CBZ_met-SD |
| 0 | 100% | 100% | 5% | 7% |
| 0.0425 | 80% | 90% | 8% | 5% |
| 0.85 | 60% | 80% | 3% | 2% |
| 1.7 | 45% | 70% | 5% | 9% |

| Sutfamethazine (SMZ) | | | | |
|---|---|---|---|---|
| MTT (µg/ml) | SMZ | SMZ-Metabolites | SMZ-SD | SMZ_met-SD |
| 0 | 100% | 100% | 6% | 8% |
| 0.0425 | 80% | 90% | 4% | 4% |
| 0.85 | 50% | 95% | 8% | 6% |
| 1.7 | 40% | 90% | 2% | 1% |

REFERENCES

Aresta A, Carbonara T, Palmisano F, Zambonin C G. 2006. Profiling urinary metabolites of naproxen by liquid chromatography-electrospray mass spectrometry. J Pharmaceut Biomed 41: 1312-1316. (Aresta, et al. 2006).

Ayala M, Batista C V, Vazquez-Duhalt R. 2011. Heme destruction, the main molecular event during the peroxide-mediated inactivation of chloroperoxidase from *Caldariomyces fumago*. J Biol Inorg Chem 16: 63-68. (Ayala et al., 2011).

Blum W, Faigle J W, faar P U, Sallmann A. 1996. Characterization of a novel diclofenac metabolite in human urine by capillary gas chromatography-negative chemical ionization mass spectrometry. J Chromatogr. B 685: 251-263. (Blum, et al. 1996).

Colonnaa, S., et al., Recent biotechnological developments in the use of peroxidases. Trends in Biotechnology 1999. 17(4): p. 163-168. (Colonnaa, et al. 1999).

Grey C E, Hedström M, Adlercreutz P. 2007. A mass spectrometric investigation of native and oxidatively inactivated chloroperoxidase. Chembiochem 8: 1055-1062. (Grey, et al., 2007)

Hager, L. P., et al., Chloroperoxidase. II. Utilization of halogen anions. The Journal of Biological Chemistry, 1965. 241(8): p. 1769-1777. (Hager, et al., 1965).

Hager, L. P., et al., Chloroperoxidase. IX. The structure of compound I. Journal of the American Chemical Society, 1972. 94(12): p. 4364-4366. (Hager, et al., 1972).

Hofrichter M, Ullrich R. 2014. Oxidations catalyzed by fungal peroxygenases. Curr Opin Chem Biol 19: 116-125. (Hofrichter and Ullrich, 2014).

Hofrichter, M. and R. Ullrich, Heme-thiolate haloperoxidases: versatile biocatalysts with biotechnological and environmental significance. Applied Microbiology and Biotechnology, 2006. 71(3): p. 276-288. (Hofrichter, et al., 2006).

Kedderis G L, Koop D R, Hollenberg P F. 1980. N-Demethylation reactions catalyzed by chloroperoxidase. J Biol Chem 255: 10174-10182. (Kedderis, et al., 1980).

Kinne M, Poraj-Kobielska M, Aranda E, Ullrich R, Hammel K E, Scheibner K, Hofrichter M. 2009. Regioselective preparation of 5-hydroxypropranolol and 4-hydroxydiclofenac with a fungal peroxygenase Bioorg. Med Chem Lett 19: 3085-3087. (Kinner, et al., 2009).

Libby, R. D., et al., Chloroperoxidase halogenation reactions. Chemical versus enzymic halogenating intermediates. The Journal of Biological Chemistry, 1982. 257(9): p. 5030. (Libby et al., 1982).

Libby, R. D., et al., Defining the involvement of HOCl or Cl2 as enzyme-generated intermediates in chloroperoxidase-catalyzed reactions. Journal of Biological Chemistry, 1992. 267(3): p. 1769-75. (Libby, et al. 1992).

Manoj, K. M., Chlorinations catalyzed by chloroperoxidase occur via diffusible intermediate(s) and the reaction components play multiple roles in the overall process. Biochimica et Biophysica Acta, 2006. 1764(8): p. 1325-1339. (Manoj, 2006).

Manoj K M, Hager L P. 2008. Chloroperoxidase, a janus enzyme. Biochem 47: 2997-3003. (Manoj, 2008).

Manoj, K. M., et al., Explaining the atypical reaction profiles of heme enzymes with a novel mechanistic hypothesis and kinetic treatment. PloS one, 2010. 5(5): p. e10601. (Manoj, 2010).

Meunier B, de Visser S P, Shaik S. 2004. Mechanism of oxidation reactions catalyzed by cytochrome p450 enzymes. Chem Rev 104: 3947-3980. (Meunier, et al., 2004).

Morris D R, Hager L P. 1966. Chloroperoxidase: I. Isolation and properties of the crystalline glycoprotein. J Biol Chem 241: 1763-1768. (Morris and Hager 1966).

Nakajima, R., I. Yamazaki, and B. W. Griffin, Spectra of chloroperoxidase Compounds II and III. Biochemical and Biophysical Research Communications, 1985. 128(1): p. 1-6. (Nakajima, et al., 1985).

Osborne, R. L., et al., *Caldariomyces fumago* chloroperoxidase catalyzes the oxidative dehalogentation of chlorophenols by a mechanism involving two one-electron steps. Journal of the American Chemical Society, 2007. 129(48): p. 14838-14839. (Osborne, et al. 2007).

Osorio V, Imbert-Bouchard M, Zonjia B, Aband J L, Perez S, Varceló D. 2014. Simultaneous determination of diclofenac, its human metabolites and microbial nitration/nitrosation transformation products in wastewaters by liquid chromatography/quadrupole-linear ion trap mass spectrometry. J Chromatogr A 1347: 63-71. (Osoria, et al., 2014).

Palcic, M. M., et al., Spectrum of Chloroperoxidase Compound I. Biochemical and biophysical research communications, 1980. 94(4): p. 1123-1127. (Palcic, et al., 1980).

Potter, D. W., D. W. Miller, and J. A. Hinson, Identification of acetaminophen polymerization products catalyzed by horseradish peroxidase. The Journal of Biological Chemistry, 1985. 260(22): p. 12174-80. (Potter, et al. 1985).

Sundaramoorthy M, Terner J, Poulosl T L. 1995. The crystal structure of chloroperpxidase: a heme peroxidase-cytochrome P450 functional hybrid. Structure 3: 1367-1377. (Sundaramoorthy, et al. 1995)

Urrea E M, Trujillo M P, Blánquez P, Vicent T, Caminal G. 2010. Biodegradation of the analgesic naproxen by *Trametes versicolor* and identification of intermediates using HPLC-DAD-MS and NMR. Bioresource Technol 101: 2159-2166. (Urrea, et al., 2010).

Urrea E M, Trujillo M P, Morató C C, Caminal G, Vicent T. 2010. Degradation of the drug sodium diclofenac by *Trametes versicolor* pellets and identification of some intermediates by NMR. J Hazard Mater 176: 836-842. (Urrea, et al., 2010).

Vázquez-Duhalta, R., et al., Biocatalytic chlorination of aromatic hydrocarbons by chloroperoxidase of *Caldariomyces fumago*. Phytochemistry, 2001. 58(6): p. 929-933. (Vazquez-Duhalta, et al., 2001).

Wang X T, Tachikawa H, Yi X W, Manoj K M, Hager L P. 2003. Two-dimensional NMR study of the heme active site structure of chloroperoxidase. J Biol Chem 278: 7765-7774. (Wang, et al. 2003).

Wojcieszyńska D, Domaradzka D, Hupert-Kocurek K, Guzik U. 2014. Bacterial degradation of naproxene-Undisclosed pollutant in the environment. J Environ Manage 145: 157-161. (Wojcieszyńska, et al., 2014).

Yi, X., et al., Examining the Role of Glutamic Acid 183 in Chloroperoxidase Catalysis. Journal of Biological Chemistry, 2003. 278(16): p. 13855-13859. (Yi, et al. 2003).

Zaks, A. and D. R. Dodds, Chloroperoxidase-catalyzed asymmetric oxidations: substrate specificity and mechanistic study. Journal of the American Chemical Society, 1995. 117(42): p. 10419. (Zaks and Dodds, 1995).

Zhang, R., et al., Spectroscopic and QM/MM investigations of Chloroperoxidase catalyzed degradation of orange G. Archives of Biochemistry and Biophysics, 2016. 596: p. 1-9. (Zhang, et al., 2016).

We claim:

1. A reaction mixture composition comprising: pharmaceutical pollutants in wastewater, or in another source of water, a remedially-effective amount of chloroperoxidase, an oxidant, a halogen ion, and a phosphate buffer, said remedially effective amount of chloroperoxidase comprising about 1.0 nM to about 50 nM chloroperoxidase, wherein said reaction mixture composition has pH value of about 2.5 to about 3.5.

2. The composition of claim 1, wherein the chloroperoxidase has a purity value of Rz=1.45.

3. The composition of claim 1, wherein the chloroperoxidase comprises growth medium of *Caldariomyces fumago*.

4. The composition of claim 1, wherein the remedially-effective amount of chloroperoxidase is about 5.0 nM to about 6.0 nM.

5. The composition of claim 1, wherein the remedially-effective amount of chloroperoxidase is about 20.0 nM to about 23.0 nM.

6. The composition of claim 1, wherein the remedially-effective amount of chloroperoxidase is about 1.0 nM to about 5.0 nM.

7. The composition of claim 1, wherein the oxidant is hydrogen peroxide.

8. The composition of claim 1, said composition comprising the oxidant at a concentration of about 0.03 mM to about 2.0 mM.

9. The composition of claim 1, wherein the halogen ion is chloride or bromide.

10. The composition of claim 9, wherein the halogen ion is chloride.

11. The composition of claim 1, wherein the halogen ion is in the form of a halide salt.

12. The composition of claim 11, wherein the halide salt is potassium chloride or potassium bromide.

13. The composition of claim 1, said composition comprising the halogen ion at a concentration of about 5.0 mM to about 25 mM.

14. The composition of claim 13, said composition comprising the halogen ion at a concentration of about 20 mM.

15. A reaction mixture composition comprising:
   wastewater, or another water source, comprising:
      chloroperoxidase at a concentration of about 0.1 nM to about 20.0 nM;
      hydrogen peroxide at a concentration of about 0.03 mM to about 2.0 mM;
      a chloride ion at a concentration of about 5.0 mM to about 25 mM; and
      a phosphate buffer; and
      one or more pollutants selected from acetaminophen, carbamazepine, sulfamethazine, diclofenac, and naproxen present in the wastewater or other water source;
   wherein said reaction mixture composition has a pH value of about 2.5 to about 3.5.

16. The composition of claim 15, said composition comprising chloroperoxidase at a concentration of about 0.5 nM to about 6.0 nM.

17. A reaction mixture composition comprising:
   wastewater, or another water source, comprising:
      chloroperoxidase at a concentration of about 20.0 nM to about 50.0 nM;
      hydrogen peroxide at a concentration of about 0.3 mM to about 0.5 mM;
      a chloride ion at a concentration of about 5.0 mM to about 25 mM; and
      a phosphate buffer; and
      one or more pollutants selected from acetaminophen, carbamazepine, sulfamethazine, diclofenac and naproxen present in the wastewater or other water source;
   wherein said reaction mixture composition has a pH value of about 2.5 to about 3.5.

18. The composition of claim 17, said composition comprising chloroperoxidase at a concentration of about 20 nM to about 23 nM.

* * * * *